United States Patent [19]

Hossack et al.

[11] Patent Number: 5,696,737
[45] Date of Patent: Dec. 9, 1997

[54] TRANSMIT BEAMFORMER WITH FREQUENCY DEPENDENT FOCUS

[75] Inventors: John A. Hossack, Palo Alto; Jian-Hua Mo, Sunnyvale; Christopher R. Cole, Cupertino, all of Calif.

[73] Assignee: Acuson Corporation, Mountain View, Calif.

[21] Appl. No.: 771,345

[22] Filed: Dec. 16, 1996

Related U.S. Application Data

[62] Division of Ser. No. 397,833, Mar. 2, 1995, Pat. No. 5,608,690.

[51] Int. Cl.$^6$ ........................................................ H04B 1/02
[52] U.S. Cl. ............................... 367/138; 367/7; 367/11
[58] Field of Search .................................. 367/103, 105, 367/138, 7, 11; 128/661.01; 73/626

[56] References Cited

U.S. PATENT DOCUMENTS

| | | |
|---|---|---|
| 3,953,825 | 4/1976 | Kino et al. . |
| 4,016,750 | 4/1977 | Green . |
| 4,140,022 | 2/1979 | Maslak . |
| 4,395,912 | 8/1983 | Hassler . |
| 4,403,311 | 9/1983 | Tournois . |
| 4,403,314 | 9/1983 | Tournois . |
| 4,446,740 | 5/1984 | Wilson et al. . |
| 4,456,982 | 6/1984 | Tournois . |
| 4,458,342 | 7/1984 | Tournois . |
| 4,550,607 | 11/1985 | Maslak et al. . |
| 4,699,009 | 10/1987 | Maslak et al. . |
| 4,870,971 | 10/1989 | Russell et al. . |
| 4,974,558 | 12/1990 | Katakura et al. . |
| 5,014,712 | 5/1991 | O'Donnell . |
| 5,105,814 | 4/1992 | Drukarey et al. . |
| 5,113,706 | 5/1992 | Pittaro . |
| 5,142,649 | 8/1992 | O'Donnell . |
| 5,218,869 | 6/1993 | Pummer . |
| 5,228,007 | 7/1993 | Murakami et al. . |
| 5,235,982 | 8/1993 | O'Donnell . |
| 5,301,674 | 4/1994 | Erikson et al. . |
| 5,322,068 | 6/1994 | Thiele et al. . |
| 5,608,690 | 3/1997 | Hossack et al. ............... 367/138 |

OTHER PUBLICATIONS

Synchronous Dynamic Focusing for Ultrasound Imaging; G. Manes, et al.; IEEE Transactions on Ultrasonics, Ferroelectrics, and Frequency Control, vol. 35, No. 1, Jan. 1988; pp. 14–21.

Properties of Swept FM Waveforms in Medical Ultrasound Imaging; C.R. Cole; 1991 Ultrasonics Symposium, pp. 1243–1248.

Frequency Synthesis by Phase Lock; William F. Egan, Ph.D., Senior Engineering Specialist GTE Products Corporation; Lecturer in Electrical Engineering Unversity of Santa Clara, Robert E. Krieger Publishing Company, Malabar, Florida 1990; pp. 14–29.

Stanford Research Systems; Synthesized Function Generator; Model DS345–30 MHz Function & Arbitrary Waveform Generator; 1994; pp. 8–13.

Stanford Research Systems; Scientific and Engineering Instruments 1994–1995; pp. 171–176.

IEEE Transactions on Ultrasonics, Ferroelectrics, and Frequency Control, vol. 37, No. 5, Sep. 1990, "Ultrasonic Nondiffracting Transducer for Medical Imaging", Jian-Yu Lu et al., pp. 438–447.

(List continued on next page.)

Primary Examiner—Daniel T. Pihulic
Attorney, Agent, or Firm—Brinks Hofer Gilson & Lione

[57] ABSTRACT

A transmit beamformer includes multiple transducers, each responsive to a respective transmit waveform to produce a respective transducer waveform. A transmit waveform generator generates the transmit waveforms, and the transmit waveforms each include multiple frequency components. Progressively higher frequency components of the transmit waveforms are timed to cause corresponding progressively higher frequency components of the transducer waveforms to focus along a line at progressively shorter ranges. In this way, a frequency dependent line focus is achieved.

75 Claims, 12 Drawing Sheets

OTHER PUBLICATIONS

IEEE Transactions on Ultrasonics, Ferroelectrics, and Frequency Control, vol. 39, No. 3, May 1992, "Experimental Verification on Nondiffracting X Waves", Jian–yu Lu et al., pp. 441–446.

IEEE Transactions on Ultrasonics, Ferroelectrics, and Frequency Control, vol. 39, No. 1, Jan. 1992, "Non–diffracting X Waves–Exact Solutions to Free–Space Scalar Wave Equation and Their Finite Aperture Realizations", Jian–yu Lu et al., pp. 19–31.

"Synthesis of the driving functions of an array for propagating localized wave energy", J.E. Hernandez et al, J. Acoust. Soc. Am. 92 (1), Jul. 1992, pp. 550–562.

"Simulated Capillary Blood Flow Measurement Using a Nonlinear Ultrasonic Contrast Agent", B. Schrope et al., Ultrasonic Imaging 14, pp. 134–158 (1992).

P. Tournois; "Acoustical Imaging Via Coherent Reception of Spatially Coloured Transmissions"; 1980 Ultrasonics Symposium; pp. 747–750.

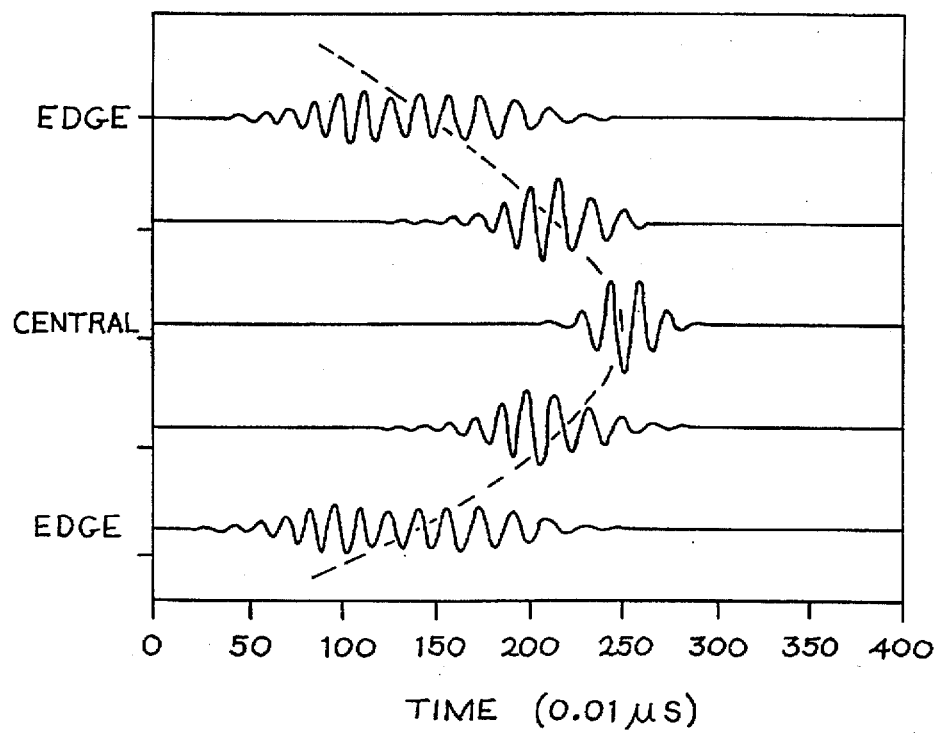
Fig. 9
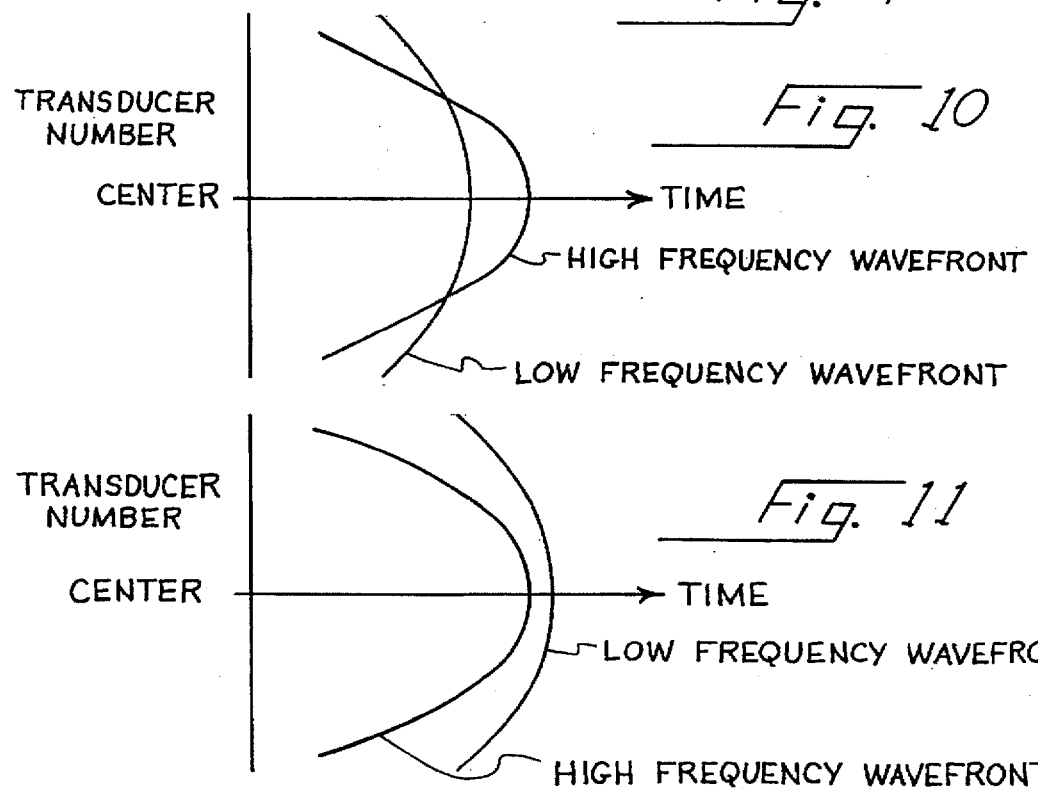
Fig. 10
Fig. 11

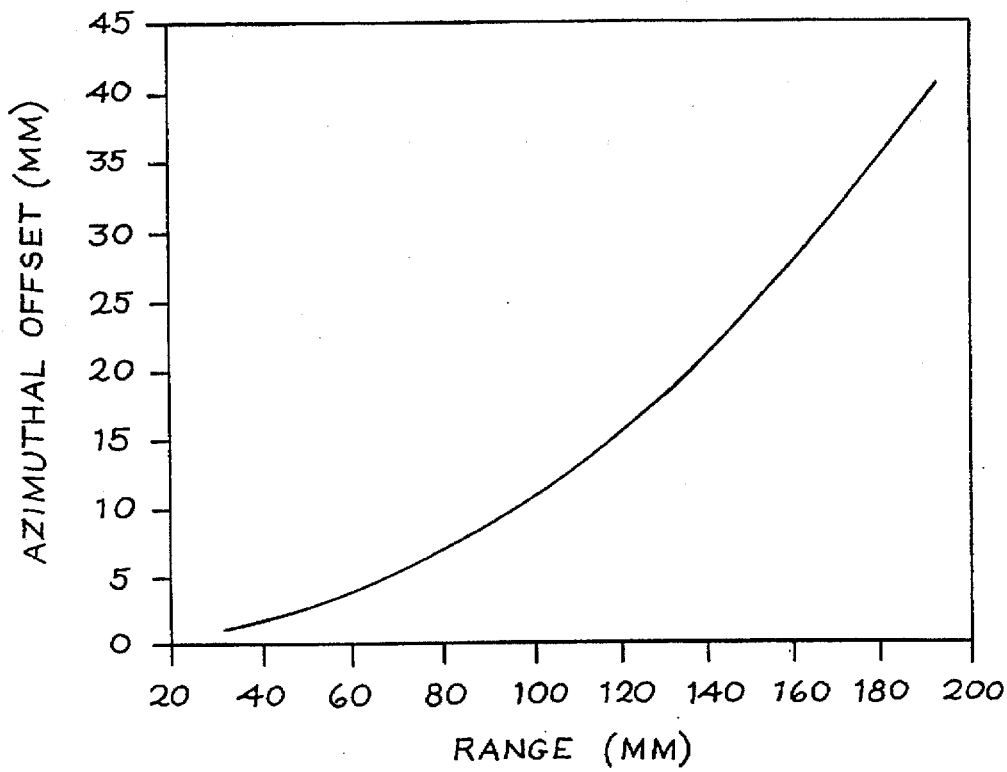
Fig. 23
Fig. 24
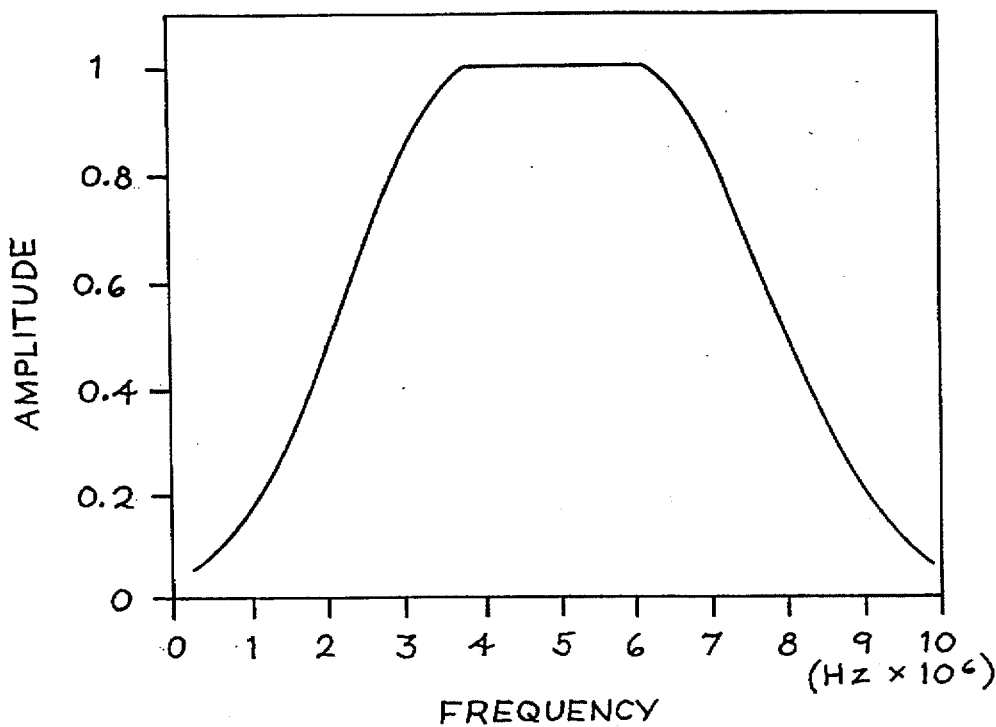

TRANSMIT BEAMFORMER WITH FREQUENCY DEPENDENT FOCUS

This application is a division of application Ser. No. 08/397,833, filed Mar. 2, 1995 now U.S. Pat. No. 5,608,690.

BACKGROUND OF THE INVENTION

This invention relates to beamformers, and in particular to a transmit beamformer that provides improved focusing.

Ultrasonic imaging is widely used in many settings, including medical applications. A typical ultrasonic imaging system includes an array of transducers, a transmit beamformer, and a receive beamformer. The transmit beamformer supplies transmit waveforms (which may be voltage waveforms) to the transducers, which in turn produce respective ultrasonic transducer waveforms (which are pressure waveforms). In a phased array system, the transmit waveforms are delayed in time to cause the ultrasonic waveforms to interfere coherently in a selected region in front of the transducers.

Structures in front of the transducers scatter ultrasonic energy back to the transducers, which generate associated receive waveforms (which may be voltage waveforms). These receive waveforms are delayed for selected times that are specific for each transducer such that ultrasonic energy scattered from a selected region adds coherently, while ultrasonic energy from other regions does not.

It is well recognized that the absorption characteristics of the body being imaged can have a significant impact on the operation of an ultrasonic imaging system. For example, the ultrasonic absorption coefficient of living tissue increases with frequency, and lower frequencies are therefore preferred for imaging at greater depths. Higher frequencies provide improved resolution in the range dimension than lower frequencies, and higher frequencies are preferred for imaging at shallower depths.

Pittaro U.S. Pat. No. 5,113,706 discloses an ultrasonic imaging system that divides the body being imaged into several zones, and uses a separate burst of ultrasonic energy at a separate frequency and power level for each zone. In this system, transmit focus and power are stepped over the entire multi-zone focal range of interest, with successive bursts that increase in focal depth, decrease in frequency, and increase in power.

One disadvantage of the system disclosed in the Pittaro patent is that multiple bursts are fired for each transducer steering position. Such multiple bursts can increase the time needed to complete an entire image. The Pittaro patent makes a brief suggestion at column 13, lines 35–39 that frequency multiplexing can be used so that the multiple wavefronts for a given steering position can be concurrent rather than successive, but no further details are given.

SUMMARY OF THE INVENTION

This invention is directed to an improved transmit beamformer that reduces or eliminates the need for multiple bursts at a given transducer steering position, and thereby increases the rate at which an image can be generated while maintaining multiple focal points.

According to this invention, a transmit beamformer generates transmit waveforms for an array of transducers, which respond by producing associated transducer waveforms. Each of at least some of the transmit waveforms comprises at least first and second frequency components which are included in a single burst of energy. The first frequency components are timed to cause corresponding first frequency components of the transducer waveforms to focus at a first, greater depth, and the second frequency components are timed to cause corresponding second frequency components of the transducer waveforms to focus at a second, shallower depth.

In the preferred embodiments discussed below, each transmit waveform includes more than two frequency components, and progressively higher frequency components of the transmit waveforms are timed to cause corresponding progressively lower frequency components of the transducer waveforms to focus at progressively greater depths.

As used herein, the term "frequency component" is meant to be interpreted broadly so as to encompass frequency components having any suitable bandwidth. Where frequency components have a finite bandwidth, they may be spaced such that adjacent components fill the bandwidth, and are therefore substantially continuous.

These embodiments allow high image-frame rates, since a single set of transmit waveforms is used to inject energy into short, intermediate and long range parts of the body being imaged. Furthermore, since the focused energy is distributed along a line, more energy may be injected into the body before power limits such as those imposed by governmental regulatory agencies are exceeded.

BRIEF DESCRIPTION OF THE DRAWINGS

FIG. 9 is a graph of the waveforms of FIG. 7 filtered through a 7 MHz bandpass filter.

FIGS. 10 and 11 are graphs showing the high and low frequency wavefronts in two alternate sets of transmit waveforms.

FIG. 23 is a graph showing the track of an ultrasound line with a radius of 500 mm.

FIG. 24 is a graph showing a modified waveform.

DETAILED DESCRIPTION OF THE PREFERRED EMBODIMENTS

The following discussion first discusses general system considerations, and then turns to a detailed discussion of individual components of the preferred system.

System Overview

Figure 1:
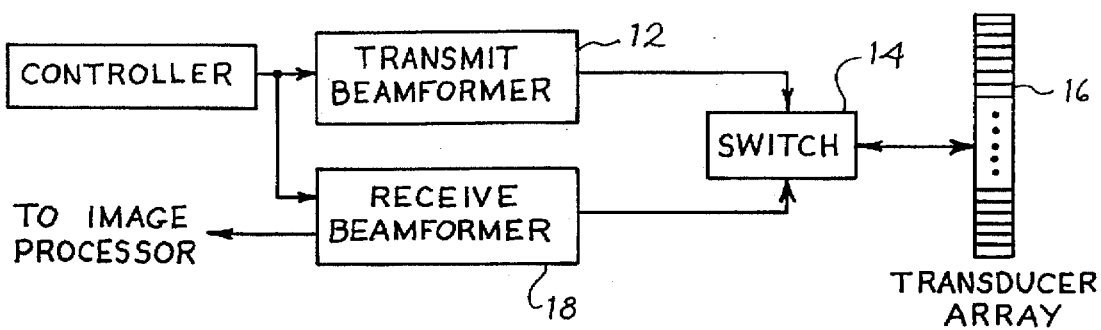
FIG. 1 is a block diagram of an ultrasonic imaging system that incorporates a presently preferred embodiment of this invention.

FIG. 1 is a block diagram of an ultrasonic imaging system which incorporates a preferred embodiment of this invention. A transmit beamformer 12 applies analog transmit voltage waveforms via a multichannel switch 14 to an array of transducers 16. The transducers 16 each receive a respective transmit waveform and generate a respective ultrasonic transducer pressure waveform. The ultrasonic transducer waveforms are timed and shaped as described below to add coherently along a selected spatial axis, with higher frequency components of the ultrasonic waveforms focused at shorter ranges (depths), intermediate frequency components focused at intermediate ranges (depths), and lower frequency components focused at longer ranges (depths). By way of example, frequency components centered at 7, 5 and 3 MHz can be focused at ranges of 40, 90 and 140 mm, respectively.

This frequency-dependent focus concentrates higher frequency ultrasonic waves at shorter ranges where they are most useful. Body attenuation increases with higher frequencies, which makes higher frequencies less useful at long ranges.

Echoes from body structures are detected by the transducers 16, which generate respective receive voltage waveforms. These receive waveforms are applied via the multichannel switch 14 to a receive beamformer 18, which applies suitable delays and filters to the receive waveforms to create a coherent sum for selected points along the spatial axis. Echoes are received sooner from closer ranges, which as explained above are associated with higher frequency components of the transmitted ultrasonic waveforms.

In one mode of operation, the receive beamformer selects delays to focus at progressively longer ranges along the line, thereby sampling multiple points along the line. In order to take advantage of the time-varying frequency distribution of ultrasonic energy along the line of focus, the receive beamformer 18 preferably includes a time-varying bandpass filter that attenuates frequency components of the receive waveforms other than those characteristic of the focal range of interest. In the above example, this bandpass filter is centered at 7, 5, and 3 MHz at times 2·40/c, 2·90/c, and 2·140/c respectively, where c is the speed of sound in the body. The center frequency of the bandpass filter varies progressively from 7 MHz at 2·40/c to 3 MHz at 2·140/c.

Transmit Waveform Determination

Transmit waveforms having the frequency-dependent focus characteristics described above can be determined as follows.

Figure 2:
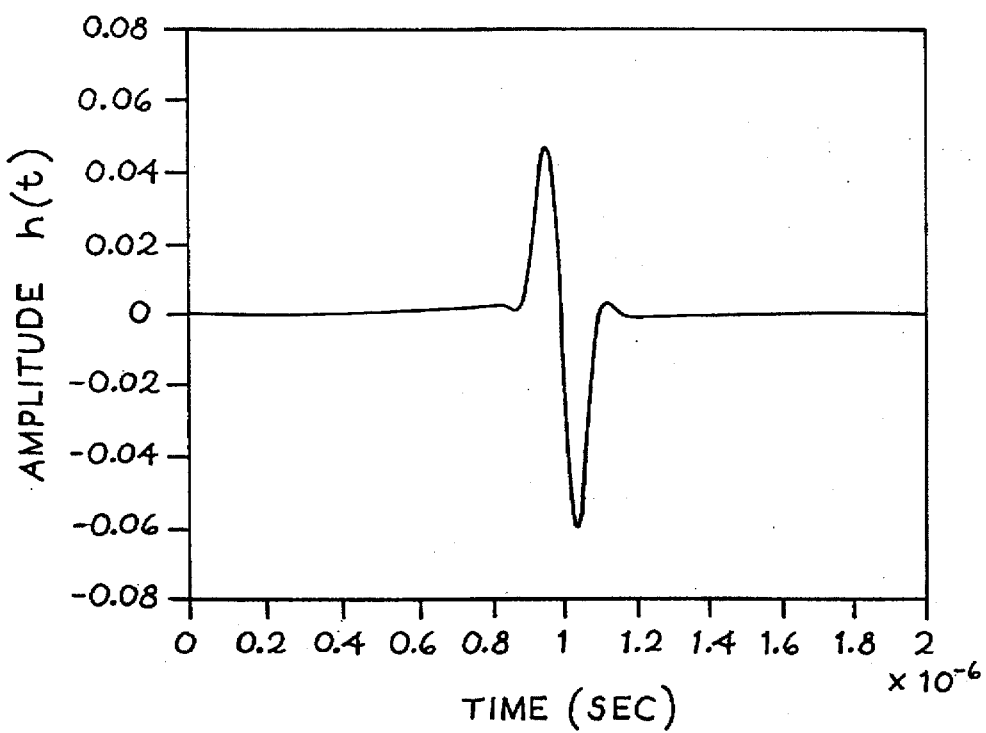
FIG. 2 is a graph of a time domain function h(t).
Figure 3:
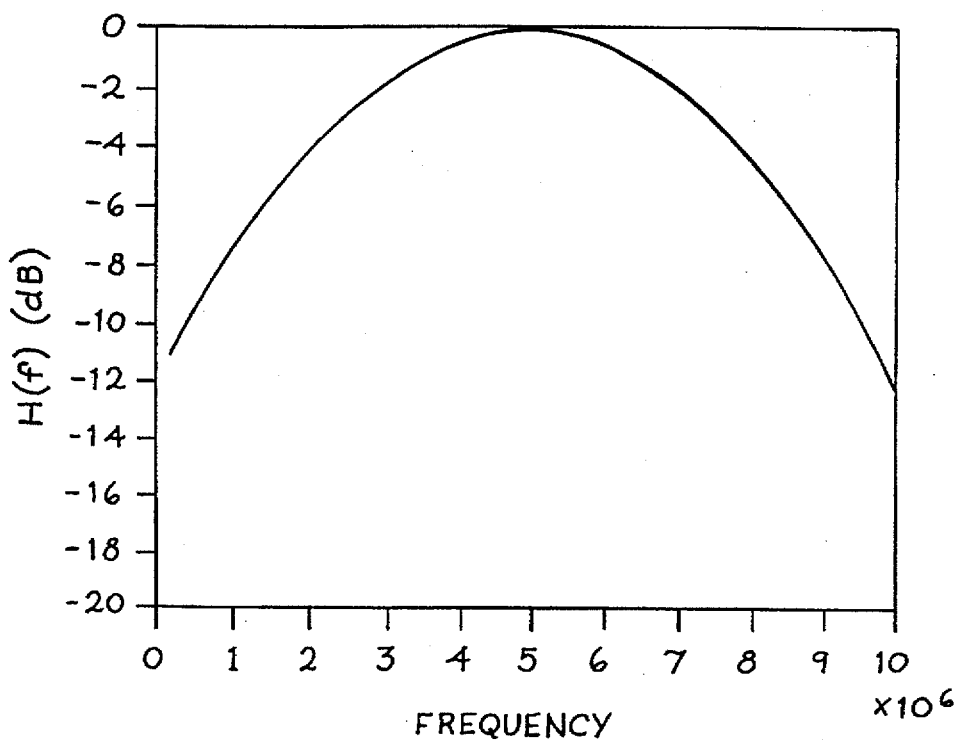
FIGS. 3 and 4 are graphs of the amplitude and phase, respectively, of a frequency domain function H(f), the Fourier transform of h(t).
Figure 4:
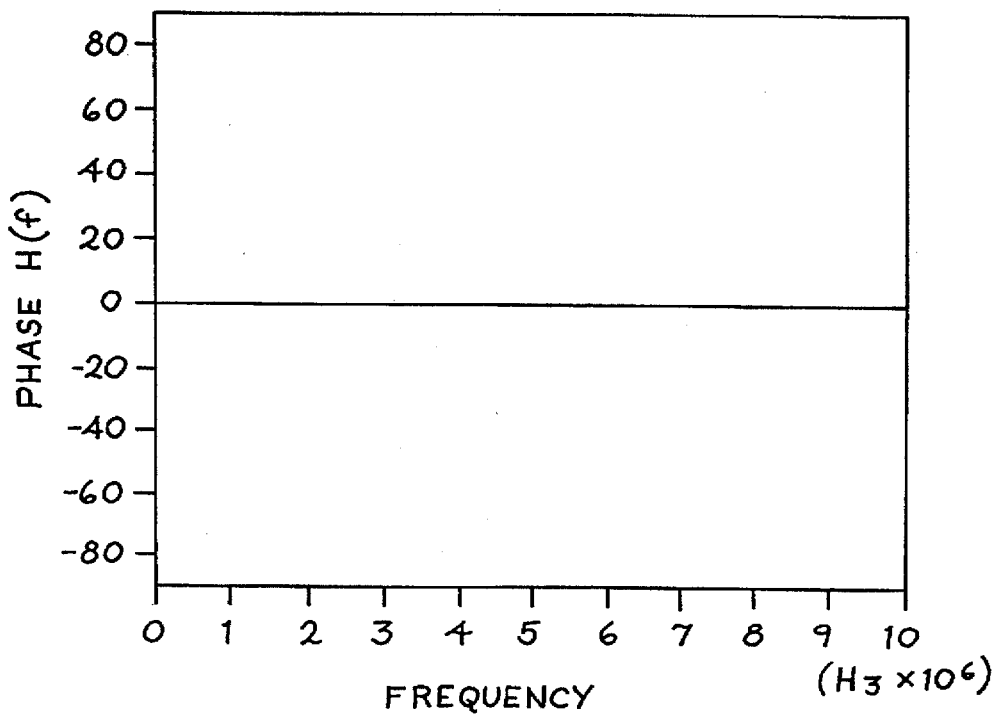

The first step is to select a starting waveform in the time domain. This starting waveform can, for example, be a pulse h(t) having a Gaussian spectrum, as shown in FIG. 2. This pulse h(t) has a fractional bandwidth of 80% at the −6 dB points, i.e., $2 \cdot (f_{HI} - f_{LO})/(f_{HI} + f_{LO}) = 80\%$, where $f_{HI}$ is the upper frequency at −6 dB with respect to the maximum level and $f_{LO}$ is the lower frequency at −6 dB with respect to the maximum level. In this specification the notation "80% −6 dB bandwidth" will be used for such a pulse. A Fourier transform is then used to convert the waveform h(t) to the frequency domain to form H(f), having amplitude and phase as shown in FIGS. 3 and 4. The starting waveform can be modified to take into account the amplitude/phase response of the transducer, as well as amplitude/phase errors in the electronics of the beamformer. For example, if the transducer is assumed to have an 80% −6 dB bandwidth, a starting waveform having a 150% −6 dB bandwidth results in a net 67% −6 dB bandwidth. Corrections for imperfections in electronics such as amplifiers and smoothing filters, and for amplitude and/or phase errors associated with potential divider effects between amplifier output impedance and transducer impedance permit less stringent specifications and therefore lower cost parts to be used.

Each frequency of interest is then assigned to a particular focal range by means of a smoothly varying function g such that Z=g(f), where Z is the focal range for the frequency f. In this example g is selected such that 3, 5 and 7 MHz are assigned to focal ranges of 140, 90 and 40 mm, respectively.

The next step is to determine the actual transmit waveform for each of the transducers and for the desired line of focus. By way of example, assume Z=40 mm, f=7 MHz, 128 transducers are arranged with a pitch of 0.15 mm, c=1.5 mm/μs, and the line of focus is normal to the transducer array and passes through the center of the transducer array.

In order to calculate the delays for the 7 MHz frequency components of each of the 128 transmit waveforms, the distance and time from transducer i to the desired focal point are calculated according to the following formulae:

$$\text{Distance} = \sqrt{X_i^2 + Z^2} ,$$

$$\text{Time} = \frac{\sqrt{X_i^2 + Z^2}}{c} ,$$

where $X_i$ equals the spacing of the $i^{th}$ transducer from the center of the transducer array.

For example, for Z=40 mm, and one of the two transducers closest to the center, $$\text{Time} = \frac{\sqrt{X^2 + Z^2}}{c} = \frac{\sqrt{(.075)^2 + 40^2}}{1.5} = 26.7 \ \mu s.$$

For Z=40 mm and the end transducer, X=(63.5×0.15 mm)= 9.52 mm and $$\text{Time} = \frac{\sqrt{X^2 + Z^2}}{c} = \frac{\sqrt{(9.52)^2 + 40^2}}{1.5} = 27.4 \ \mu s.$$

Thus, the 7 MHz component of the end transducer must be advanced by 27.4−26.7=0.7 μs with respect to the 7 MHz component of the central transducers. In this context, 'advanced' equals 'negative delayed'. This delay can be accomplished in the frequency domain by multiplying H(f) by $e^{-j2\pi ft}$, where t=−0.7 μs and f=7 MHz for this particular frequency component. The process is repeated for all transducers and all frequency components (and associated focal ranges) of interest.

The foregoing example relates to a center scan line that is straight and normal to the transducer array. A similar approach can be used for off-center and curved scan lines, as long as $X_i$ and Z are selected properly. That is, the range calculation should use $X_i$ and Z as measured from the intended focal point to the $i^{th}$ transducer. By positioning the intended focal point properly, delays for angled scan lines and curved scan lines can readily be determined.

In many cases it will be preferable to avoid negative delays (advances) that imply transmit waveforms having non-zero values before t=0. This can be done by calculating the greatest expected end-to-center delay difference for the entire transducer array. This greatest delay difference generally occurs at the nearest focal distance, and is assigned as a constant denoted Delay_Max. The required time advances (negative delays) discussed above may now be added to Delay_Max to determine the time value to be used in the frequency domain delay operations, thereby avoiding all negative delays. Of course, any constant value greater than Delay_Max is also suitable.

Figure 5:
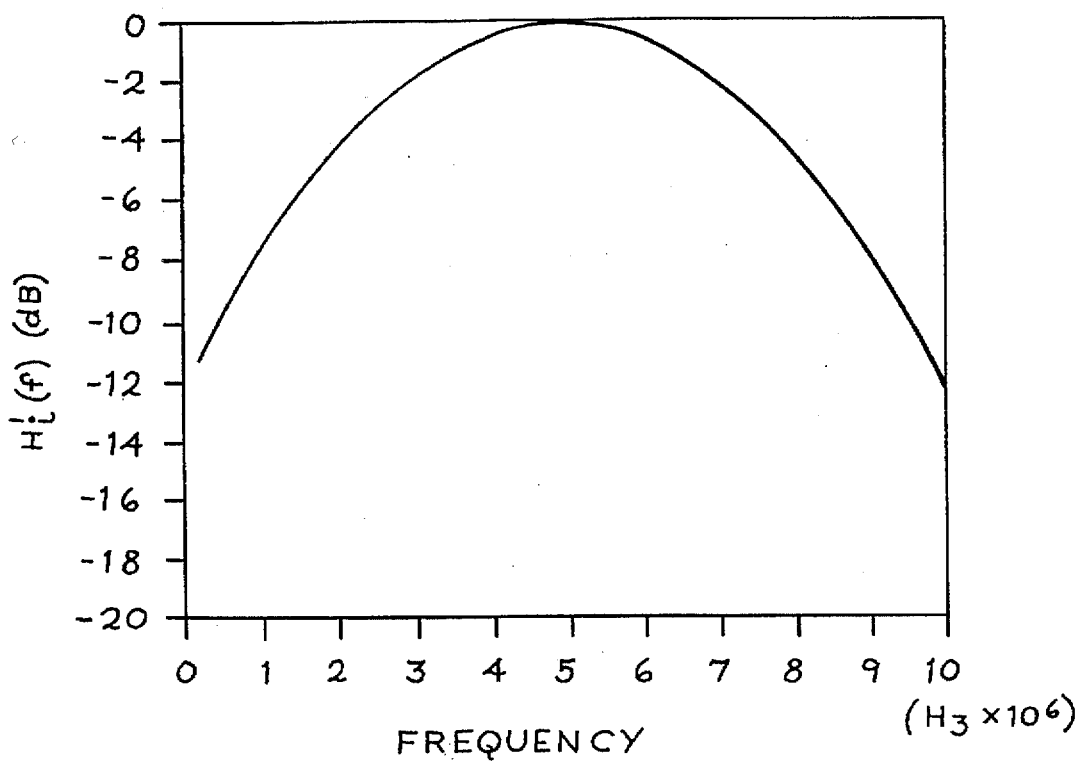
FIGS. 5 and 6 are graphs of the amplitude and phase of a time shifted frequency domain function $H'_i(f)$.
Figure 6:
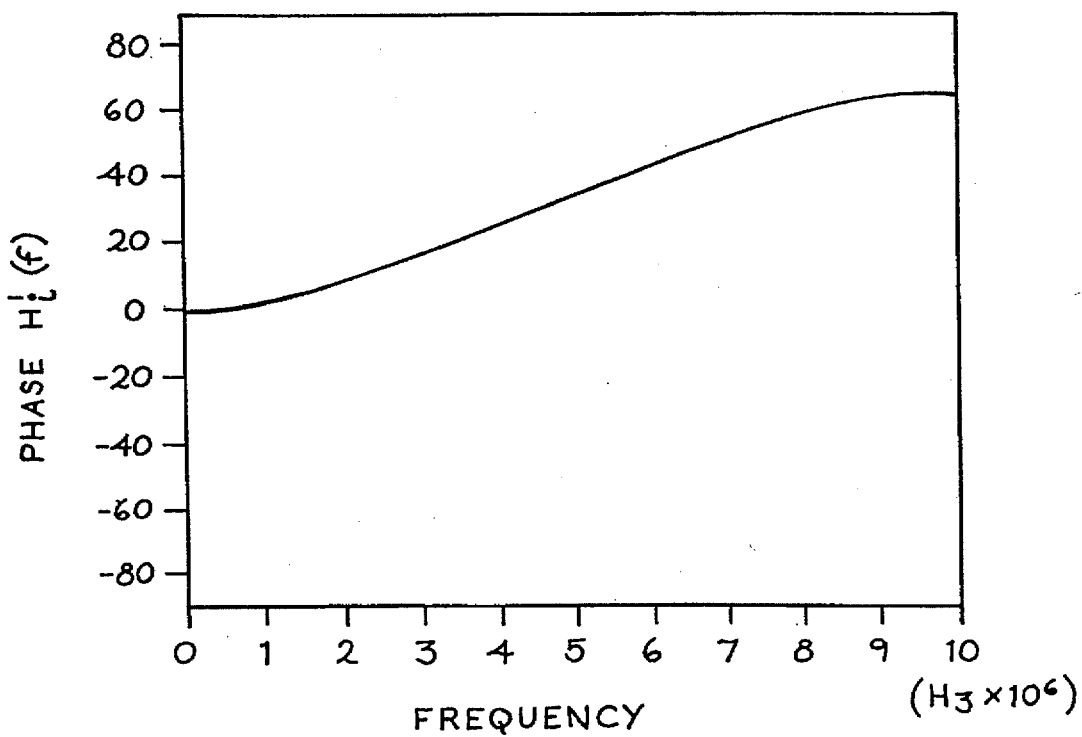

This process is repeated for all frequencies for the $i^{th}$ transducer to produce $H'_i(f)$, having the amplitude and phase shown in FIGS. 5 and 6, respectively. The frequency domain function $H'_i(f)$ is then converted by use of an inverse Fourier transform to form the time domain function $h'_i(t)$, which is the transmit waveform for the $i^{th}$ transducer.

Figure 7:
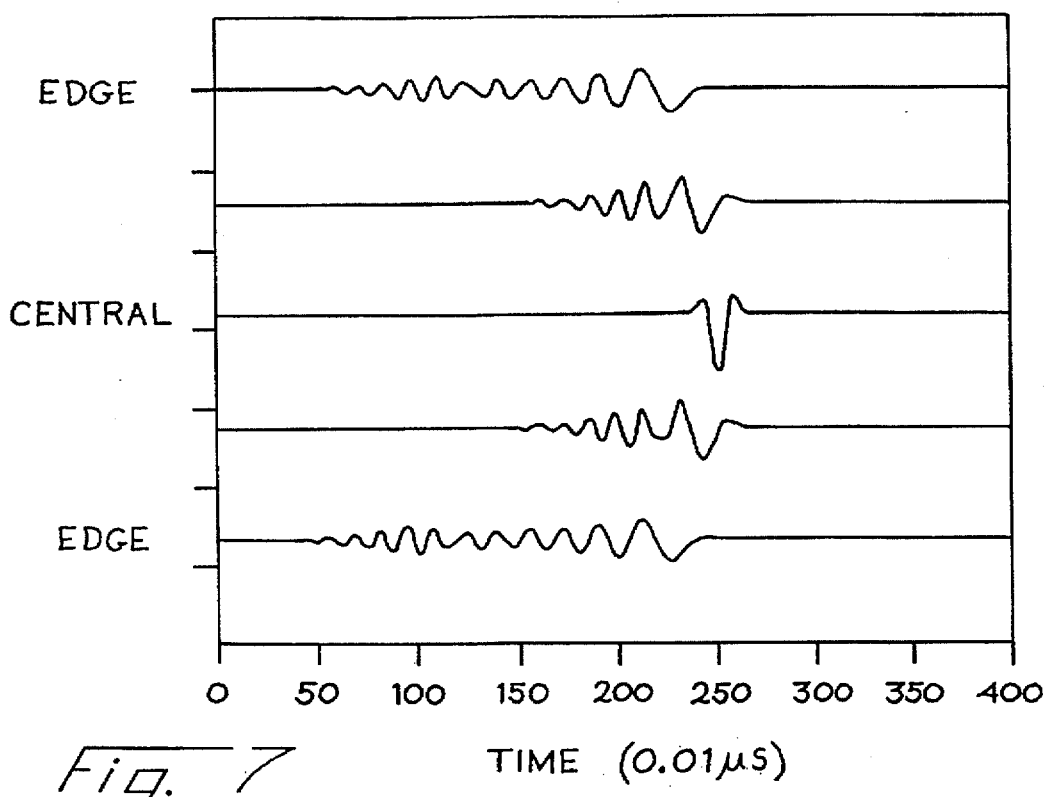
FIG. 7 is a graph showing the time development of selected transmit waveforms.
Figure 8:
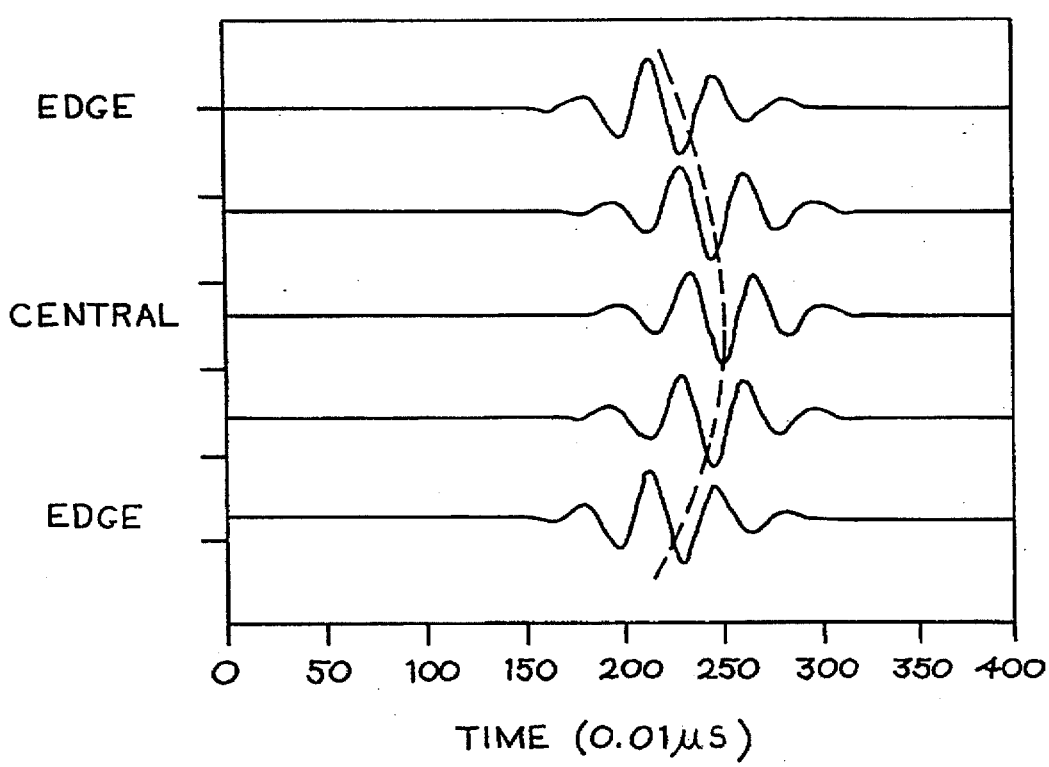
FIG. 8 is a graph corresponding to the waveforms of FIG. 7 filtered through a 3 MHz bandpass filter.

FIG. 7 shows the transmit waveforms for five of the transducers $h_0, h_{31}, h_{63}, h_{95}, h_{127}$, where $h_0$ and $h_{127}$ are the transmit waveforms for the end transducers, and $H_{63}$ is the transmit waveform for one of the two central transducers. Note that in each case all of the frequency components in any one transmit waveform are combined in a single burst of energy or a single frequency modulated pulse signal, rather a sequence of multiple unmodulated pulses. Each transmit waveform is a continuously, constantly varying signal, rather than multiple pulses separated by a non-varying period lasting more than two times the period of the lowest frequency within the −6 dB bandwidth of the transmit waveform. FIG. 8 shows the transmit waveforms of FIG. 7 filtered with a bandpass filter centered at 3 MHz. The dotted line in FIG. 8 shows the curved wavefront of the 3 MHz components, that causes these lower frequency components to focus at the long range of 140 mm. FIG. 9 shows the transmit waveforms of FIG. 7 filtered with a bandpass filter centered at 7 MHz. The dotted line in FIG. 9 shows the more deeply curved wavefront of 7 MHz components, that causes these higher frequency components to focus at the short range of 40 mm.

Note that the transmit waveform for each transducer includes a wide range of frequency components, and the delays for individual frequency components are selected such that the separate frequency components of each transmit waveform are focused at respective focal ranges. The transducer waveforms produced by the transducer array as a whole generate a continuous line focus rather than a point focus, and differing frequency components are focused at differing ranges or depths along the line. At least for some of the transmit waveforms, the various frequency components are contained in a single burst of energy.

The foregoing discussion illustrates only one approach to determining the transmit waveforms. Many modifications and alternatives are possible, including the following.

The transmit waveforms may be shaped to reduce the effect of ringing in the waveforms of the transducers at the end of the array by using conventional aperture apodization techniques to emphasize the response of the center elements at the expense of the end elements. Low-pass filtering may be used on the transmit waveforms for the end elements to suppress high frequency ringing, which is largely due to rapidly changing phase at higher frequencies. Additionally, higher frequency components may be focused at longer ranges for the end transducers than for the center transducers. It is often not necessary to focus any part of the pressure wave from end elements at extremely close ranges, and by focusing all of the pressure wave from end elements at longer ranges, high phase changes and associated ringdown can be reduced.

Additionally, the delay profile can be continued down to 0 Hz and up to beyond 10 MHz. Beyond the upper band edge of the transducer, it may be disadvantageous to continue to reduce the focal distance at a constant rate. A minimum focal range can be defined, which higher frequencies approach asymptotically. As mentioned above, the near focal limit may not be the same for the end transducers as for the center transducers.

The transmit waveforms may additionally be designed to compensate for beamforming distortions. For example, since different frequency components are attenuated by different amounts in the body, low frequency components may be enhanced in amplitude to increase the energy focused at long range targets. To the extent that the effective velocity of ultrasonic waves in the body varies with frequency, such variations can be taken into account in calculating the delays used in determining the transmit waveforms.

It is known in the art that lower frequencies can be used for off-axis ultrasound scan lines to reduce the adverse effect of grating lobes due to undersampling at high frequencies for wide element spacing. This approach can readily be used in determining the transmit waveforms for such scan lines.

The previous discussion has related to the objective of producing temporally compact wave-forms along the scan line. In certain applications it is desirable to produce temporally long waveforms. Coded waveforms of the type described by M. O'Donnell in IEEE Trans. UFFC Vol. 39, No. 3, pp. 341–351 may also be used with this invention. These waveforms, which are essentially 'chirp' waveforms, have the advantage of higher signal to noise since they increase pulse energy without increasing peak power and hence take advantage of the fact that regulatory limits on peak acoustic power are more burdensome than the limits on peak acoustic energy in this application. (Signal to noise is related more to signal energy than signal power). Since the different frequency components are focused to different points, the nature of the focused waveform will vary with range. Nevertheless, by filtering to a reduced bandwidth (e.g., 30% −6 dB fractional bandwidth), the resultant waveform will contain well focused components. Another feature of 'chirp'-like waveforms is that if the low frequencies occur earlier than the high frequency components, the total temporal spread in the waveforms applied to the end elements may be reduced. FIG. 10 illustrates the high and low frequency components in such a case. Note that the total delay from the start to finish of the transmit waveforms is reduced in FIG. 10 as compared to FIG. 11, which shows the alternate relationship.

In the present invention, a preferred 'chirp' waveform my be developed as follows for substitution in place of the starting waveform illustrated in FIG. 2. The design of this 'chirp' waveform scales the incremental delay between successive frequency components with the period of the particular frequency component. These delays are applied to the frequency components making up the original pulse, which my, like the pulse illustrated in FIG. 2, have a Gaussian spectral envelope and linear phase for all frequency components. For simplicity, the current discussion considers a discretely sampled spectrum comprising frequency samples at f(j), where f(j) is the frequency of the jth sample. Generally, waveforms in this invention are continuous in both the time and frequency domains. This condition may be obtained by letting discrete sample intervals tend to infinitesimally small values.

$$\text{Delay}(j) = \frac{\sqrt{X^2 + Z^2} - Z}{2 \cdot N \cdot c} \cdot \frac{f_c}{f_{(j)}} + \text{Delay}(j-1),$$

$$\text{where } X = \frac{n-1}{2} \cdot \text{pitch},$$

n=number of elements in the transducer array,
Z=near focal distance for high chosen frequency component (40 mm in this example),
N=number of frequency samples between low frequency component $f_{LO}$ (3 MHz in this example) and high frequency component $f_{HI}$ (7 MHz in this example),
$f_c$=center frequency =5 MHz in this example,
$f_{(j)}$ =frequency of $j^{th}$ sample.

Delays are calculated over the range $0.3 \cdot f_{LO}$ to $2 \cdot f_{HI}$, where $f_{LO}$=3 MHz and $f_{HI}$=7 MHz in this example. Delays for samples where f(j) is less than $0.3 \cdot f_{LO}$ are set equal to zero. Delays for samples where f(j) is greater than $2 \cdot f_{HI}$ are set equal to the delay for the sample corresponding to $f(j)=2 \cdot f_{HI}$. A chirp waveform has the advantage that energy is spread out in time and hence peak power is lowered, reducing the risk of exceeding government regulated power levels.

The waveforms corresponding to a number of separate ultrasound lines can be calculated and then summed prior to application to the transducers such that ultrasonic energy is focused along several different scan lines. The transmit scan lines may be straight or curved, as desired. If the transmit scan lines are curved, the azimuthal position of the focus varies with range and frequency. The receive beamformer would preferably accommodate this change, and the scan converter would write to X-Y locations using curved rather than straight line acoustic data. As an example, in the scan converter described by S. C. Leavitt et al. 'A Scan Conversion Algorithm for Displaying Ultrasound Images' (Hewlett-Packard Journal, October 1983, pp. 30–34), the X-Y Raster State Machine (page 33) could be programmed with a sequence of X-Y pixel addresses following a curved rather than straight trajectory. Also, each transmit scan line may be spread out in width. For example, in some applications it may be preferable to spread or defocus the beam to a width such as 4° to allow multiple receive scan lines for a single transmit scan line.

Transmit Beamformer

Figure 12:
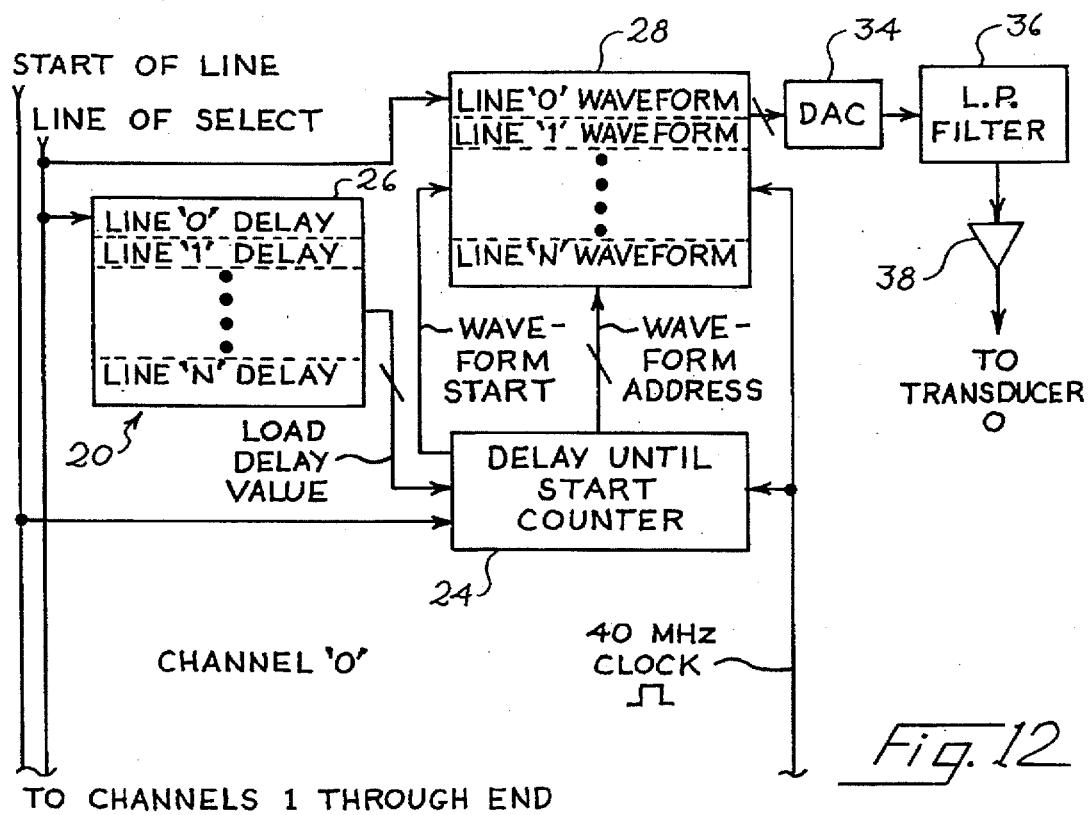
FIG. 12 is a block diagram showing a first preferred embodiment of the transmit beamformer

Once the desired transmit waveforms have been determined as discussed above, the transmit beamformer 12 can be implemented as shown in FIG. 12 to generate the previously determined transmit waveforms.

The transmit beamformer 12 includes N channels, one for each of the transducers 16 (FIG. 1). Each channel includes a delay memory 20, a waveform memory 22, and a delay counter 24 (FIG. 12). The delay memory 20 includes 256 words 26, one for each possible steering angle or ultrasound scan line. The waveform memory 22 includes 256 sections 28, one for each possible steering angle. Each word 26 is set equal to a negative number equal to the number of clock cycles that elapse between a start of line signal and the first non-zero value of the associated waveform. For simplicity, it is assumed that zero is defined as the most significant bit equal to 1 and all other bits equal to 0. Hence, the most significant bit becomes an enable signal for the memory. Each section 28 stores a respective waveform, for example as 64 or 128 successive eight bit words. When a section 28 is read with a 40 MHz clock, the resulting sequence of digital values defines a waveform approximately 1.6 to 3.2 µs in duration. The delay memory 20 is not required, but it reduces memory requirements for the waveform memory 22. This is because the delay memory 20 eliminates the need to store a large number of leading zeros when the ultrasound line is steered at a large angle.

In use, each channel responds to a scan line selection signal on line 30 by loading the word 26 for the selected scan line into the delay counter 24, and by enabling the selected section 28 of the waveform memory 22. Typically, each word 26 stores a negative binary integer equal to the desired delay before the first non-zero value of the respective waveform.

The delay counter 24 responds to a start of scan line signal on line 32 by incrementing the stored value with each cycle of a 40 MHz clock. When the counter 24 increments to zero, it enables the waveform memory 22. Subsequently generated values of the counter 24 (incrementing now from zero upwards) become address values for the memory 22. As each word of the section 28 for the selected scan line is addressed, the corresponding eight bit word is read and applied to a digital-to-analog converter 34. The analog output signal of the converter 34 is passed through a low-pass filter such as a Bessel filter 36 to reduce sampling effects and then to an amplifier 38. The output of the amplifier 38 is the transmit waveform discussed above that is applied to the respective transducer 16 via the multichannel switch 14 (FIG. 1).

In general, there is considerable similarity between waveforms applied to adjacent transducers 16 and between waveforms of adjacent lines. A number of approximations can be used which take advantage of the redundancy in the information stored in the waveform memory 22 to reduce memory requirements.

Figure 13:
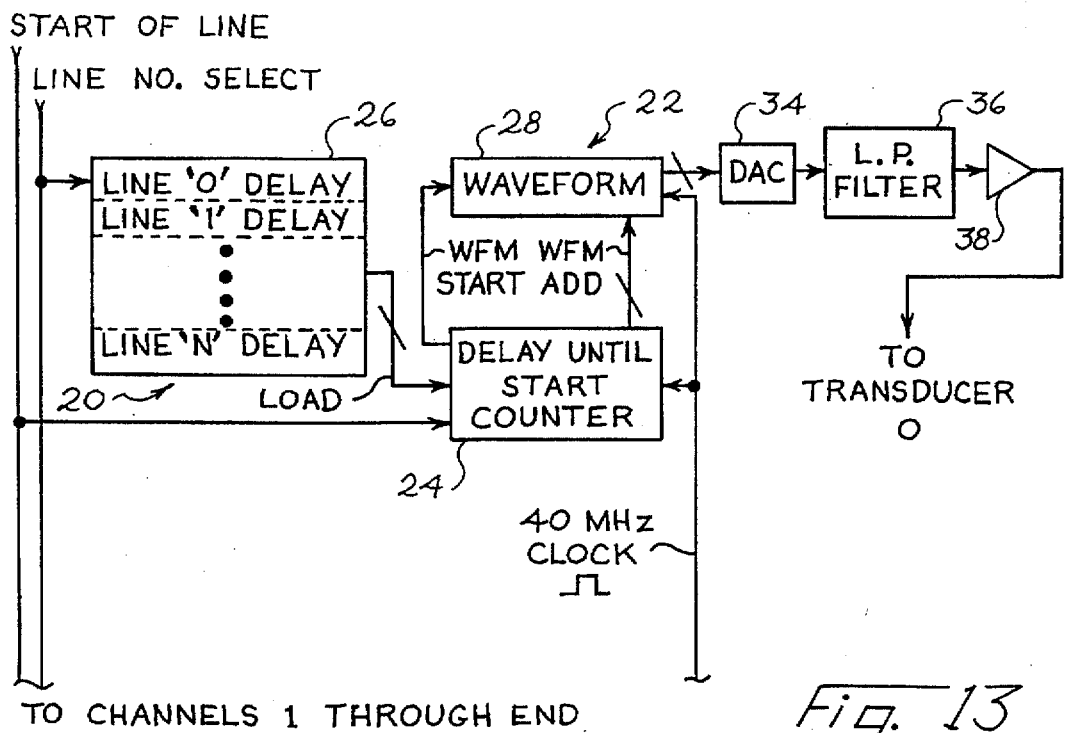
FIG. 13 is a block diagram showing a second preferred embodiment of the transmit beamformer 12.

Another approach is shown in FIG. 13, which includes many of the same components as those discussed above in conjunction with FIG. 12. The central difference between the systems of FIGS. 12 and 13 is that each transducer channel of the system of FIG. 13 uses only a single waveform memory section 28 that stores only a single waveform made up of 64 or 128 eight bit words. The waveform stored in the waveform memory section 28 may be the waveform calculated for the center scan line. The system of FIG. 13 functions as described above in conjunction with FIG. 12, except that the scan line number select signal does not select one of multiple waveform memory sections. All of the waveforms for all of the ultrasound scan lines are identical in shape. They differ from one another only in that linear delays are applied to successive scan lines to effect scan line steering.

When the approach of FIG. 3 is used it should be understood that as each scan line is steered farther from the central scan line perpendicular to the transducer array, an error in the focusing component causes the focal points to approach the transducers by a factor of $(\cos\theta)^2$, where θ is the steering angle measured with respect to the perpendicular. This focusing error results from the fact that the effective pitch between adjacent transducers is modified by $\cos\theta$ for nonperpendicular steering angles, and the resulting delay is modified by $(\cos\theta)^2$.

As an improvement to compensate partially for this effect, one can calculate the delays required to focus at the desired range (for example 140 mm). One can then calculate the delays required to focus at 70 mm (i.e. the range to which the beam is actually focused if it was originally focused at 140 mm but has been steered to 45°). The difference in the delays for 140 mm and 70 mm can be applied to the waveforms discussed above to compensate for this focusing error. This correction applies exactly only to one frequency component, and other frequency components (and associated other ranges) will not be exactly corrected.

Figure 14:
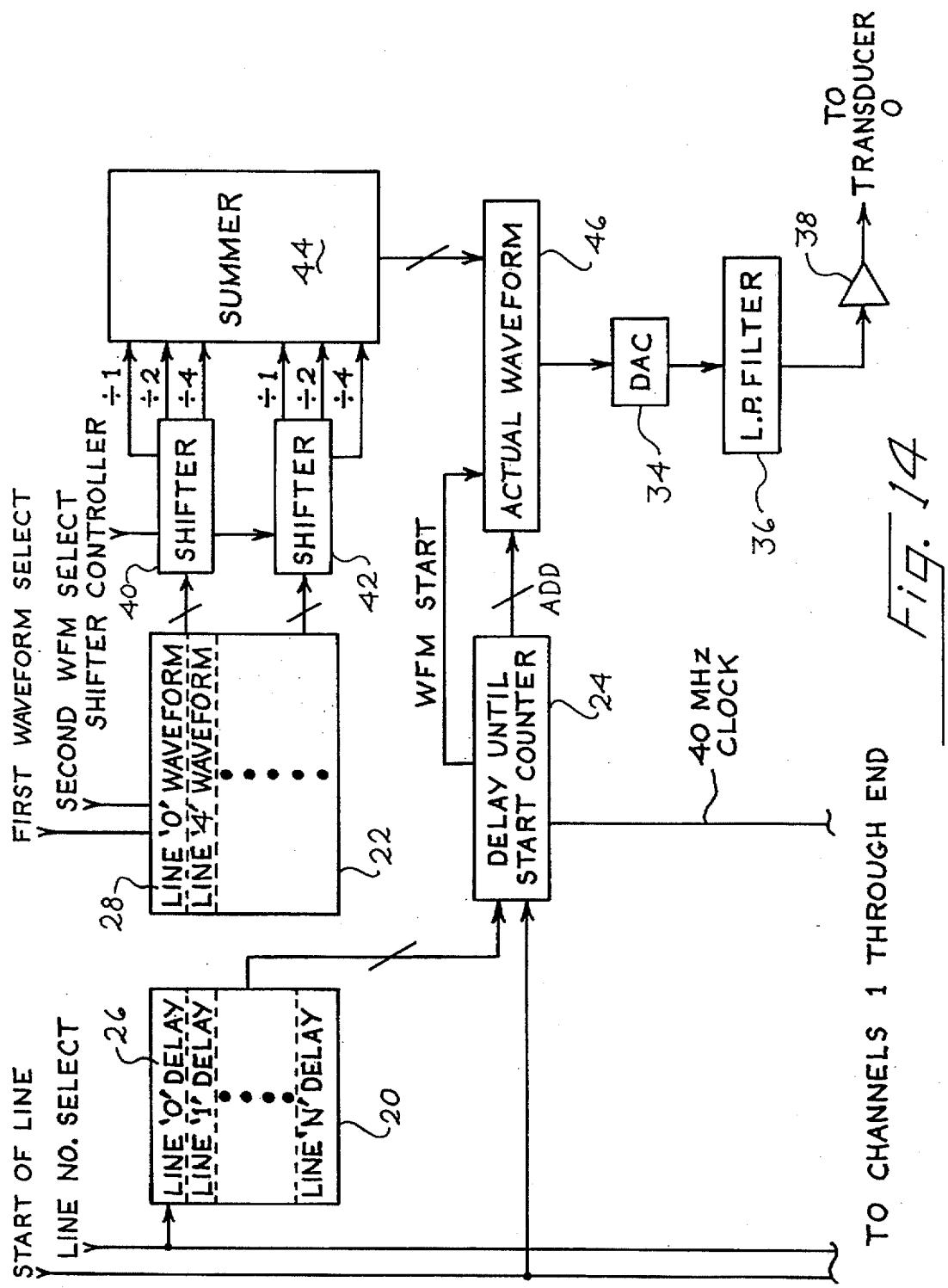
FIG. 14 is a block diagram showing a third preferred embodiment of the transmit beamformer 12.

FIG. 14 shows another system that uses an interpolator to reduce memory requirements as compared to the system of FIG. 12. In the system of FIG. 14 the delay memory 20, the delay counter 24 and the components 34, 36 and 38 are as described above. In this case the waveform memory 22 includes sections 28 that store only every fourth (or other power of two) waveform for the respective transducer. The actual waveform used by intermediate lines is interpolated digitally using the shifters 40, 42, the summer 44 and the actual waveform memory 46.

A central controller provides first and second waveform select signals which select the two waveforms to be used for the interpolation. This controller also generates shifter control signals. The first waveform identified by the first waveform select signal is applied to the first shifter 40, and the second waveform identified by the second waveform select signal is applied to the second shifter 42. Each of the shifters 40, 42 supplies outputs equal to selected ones of the following: the corresponding waveform divided by 1, the corresponding waveform divided by two, and the corresponding waveform divided by four. The outputs of the shifters 40, 42 can be obtained at high speed by simple shifting operations. The summer 44 sums the various signals generated by the shifters 40, 42 to generate the actual waveform, which is stored in the actual waveform memory 46.

This actual waveform memory 46 stores 128 eight bit signals. The delay counter 24 is loaded with the appropriate delay from the delay memory 20, and then clocked beginning at the start-of-scan-line signal. When the value in the delay counter 24 goes positive, it addresses consecutive words in the actual waveform memory 46 and applies them to the digital-to-analog converter 34.

Table 1 provides further information regarding the operation of the waveform memory 22 and the shifters 40, 42.

TABLE 1

| Line No. | First Waveform Select Signal | Second Waveform Select Signal | Shifter 40 | | | Shifter 42 | | |
|---|---|---|---|---|---|---|---|---|
| | | | +1 | +2 | +4 | +1 | +2 | +4 |
| 0 | 0 | 4 | 1 | 0 | 0 | 0 | 0 | 0 |
| 1 | 0 | 4 | 0 | 1 | 1 | 0 | 0 | 1 |
| 2 | 0 | 4 | 0 | 1 | 0 | 0 | 1 | 0 |
| 3 | 0 | 4 | 0 | 0 | 1 | 0 | 1 | 1 |
| 4 | 4 | 8 | 1 | 0 | 0 | 0 | 0 | 0 |
| 5 | 4 | 8 | 0 | 1 | 1 | 0 | 0 | 1 |

As shown in Table 1, for scan lines 0–3 the scan line 0 and 4 waveforms are applied to the shifters 40, 42, respectively. Scan line 0 is equal to the waveform stored in scan line 0 of the waveform memory 28, because only the +1 output of the shifter 40 is enabled. Similarly, scan line 1 is equal to the sum of ½ plus ¼ of the waveform for scan line 0 plus ¼ of the waveform for scan line 4. The waveform for scan line 2 is equal to ½ the waveform for scan line 0 plus ½ of the waveform for scan line 4.

Since the delay between adjacent scan lines is at least 50 microseconds for a target at a distance of 40 mm, there is sufficient time to accomplish simple digital interpolations using shifts, which can be hardwired, and selected adds of shifted components from adjacent lines.

Interpolated waveforms can also be determined by generating two digital waveforms, converting them to their analog counterparts, and then performing the desired interpolation as a weighted analog sum using controlled gain amplifiers and a summer. This approach is an analog version of the system of FIG. 14. It is possible to use interpolation techniques similar to those of FIG. 14 to interpolate between successive transducers. Also, it is possible to store only a limited set of waveforms (either for a limited set of lines and/or a limited set of transducers). One would use the closest stored waveform for transducers and/or lines which are not explicitly stored. The extent of hardware simplicity afforded by this technique is balanced with a slight loss of performance.

Figure 15:
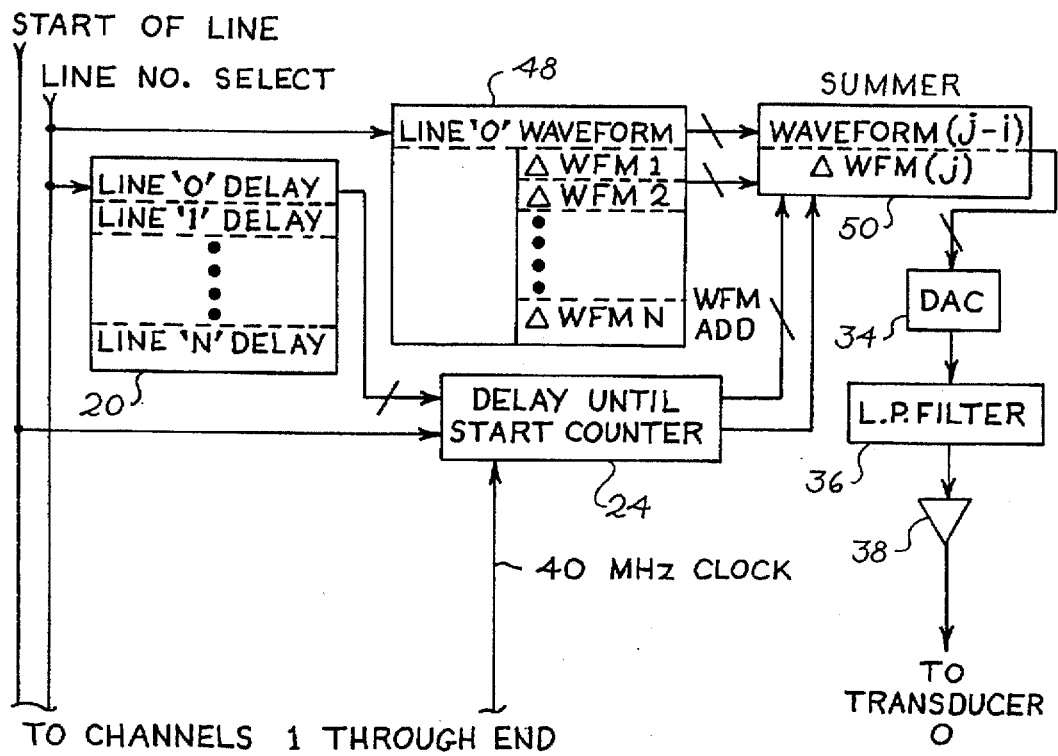
FIG. 15 is a block diagram showing a fourth preferred embodiment of the transmit beamformer 12.

FIG. 15 relates to another system which takes advantage of the fact that there is considerable redundancy between the waveforms applied to adjacent scan lines for any given transducer. As shown in FIG. 15, the waveform memory 48 stores the complete waveform for a given transducer, such as the waveform for scan line 0. A value $\Delta$WFM is stored for each subsequent scan line. The summer 50 is initially loaded with the waveform for scan line 0, and $\Delta$WFM1, $\Delta$WFM2, . . . $\Delta$WFMN are then successively added. In each case $\Delta$WFMn is the increment between the waveform for scan line (n−1) and the waveform for scan line n. The contents of the summer 50 represent the actual waveform for the transducer of interest and the corresponding scan line. This actual waveform is clocked by the delay counter 24 into a digital-to-analog converter 34. For example, the summer 50 can add the waveform for scan line 1 to the value of $\Delta$WFM for scan line 2 to generate the actual waveform for the second scan line and the respective transducer. The approach of FIG. 15 is especially well suited for use in systems in which scan lines are fired in consecutive order. The basic approach illustrated in FIG. 15 can be adapted for successive transducers instead of or in addition to successive scan lines.

Arbitrary waveforms of the type described above can be generated with conventional function generators, such as the Model DS345 synthesized function generator of Stanford Research Systems. An array of such devices is a practical approach to implementing the transmit beamformer 12 in the shortest amount of time, particularly when a smaller number of transducers such as sixteen is used.

Since the capacity of the GPIB which connects a computer to several DS345's is limited, it may be necessary to use more than one computer and build the beamformer with subarrays with separate computers and GPIB's. This system is still practical since once all the DS345's in the different subarrays have been programmed they can be triggered from a single external synchronizing source.

There are other means for generating approximations to the waveforms discussed above. One approach is to produce a square wave burst with a period between successive transitions that determines the fundamental frequency. A low-pass filter can be applied to remove the harmonics and to smooth the waveform to make it more like one of the waveforms discussed above. This technique would also achieve the effect of focusing various frequency components at various respective ranges.

It is anticipated that the programmable waveform transmit beamformer described in Cole et al. U.S. patent application Ser. No. 08/286,652, filed Aug. 5, 1994, now abandoned and assigned to the assignee of the present invention can be adapted for use with this invention.

Transducers

A wide variety of transducers 16 can be used, and this invention is not limited to the linear transducer array discussed above. The techniques discussed above of delaying separate frequency components (so as to achieve a multiple focal ranges) may be applied to two dimensional arrays having M azimuth elements and N elevation elements, or to a 1.5 dimension array which will typically have a small number of elements in the elevation direction, such as 3, 5 or 7.

A plano-concave transducer array can be used in which different frequency components are focused at different ranges in elevation. See for example the discussion in the continuation in part of Hanafy U.S. patent application Ser. Nos. 08/117,869 and 08/117,868, filed Sep. 7, 1993, now U.S. Pat. Nos. 5,438,998 and 5,415,175.

The Receive Beamformer

The receive beamformer 18 preferably includes a dynamic receive focusing system that allows the focus of the receive beamformer to be changed at a high rate in order to follow as accurately as possible the range along the ultrasonic scan line corresponding to the currently arriving signals.

Preferably, the receive beamformer 18 includes a time-varying adjustable bandpass filter which is adjusted in real time to emphasize the frequency of the currently arriving signals. Green U.S. Pat. No. 4,016,750 describes a simple analog implementation for such a time-varying filter. A high-pass filter can be substituted for a bandpass filter. The body acts as a low-pass filter, and for this reason a high-pass filter may be sufficient to achieve the desired effect.

When a time-varying bandpass filter is used, it can slide from above 7 MHz to below 3 MHz if desired. The slide rate function need not be uniform with respect to time. The optimum bandwidth and filter characteristics of the sliding filter can best be determined from experience and by using design tools. A narrow bandwidth will give higher focusing accuracy but relatively poor axial (range) resolution due to ring down. The frequency downshift related to natural body attenuation should be taken into account in the design of such a filter.

Heterodyne time-varying filters may also be used in the receive beamformer 18. Analog ultrasound systems frequently use a heterodyne technique to shift radio frequency pulses generated by the transducer down to an intermediate frequency, e.g. 1–3 MHz. See for example Maslak U.S. Pat. No. 4,140,022, and Pummer U.S. Pat. No. 5,218,869. If a narrow bandpass filter is employed on an intermediate frequency signal of 2 MHz, a time-varying bandpass filter will be formed which only passes components corresponding to the original components of 7 MHz down to 3 MHz as the local oscillator is varied from 9 MHz to 5 MHz. A time-varying local oscillator my be realized by using a voltage controlled oscillator circuit, where the voltage determining the desired local oscillator frequency is derived via a digital-to-analog converter from a value supplied by the system computer controller.

A-time-varying, sinusoidal-frequency waveform may also be generated using any one of a number of digital synthesizer techniques. See W. F. Egan, "Frequency Synthesis by Phase Lock", Krieger, 1990.

Digital filtering can also be used in the receive beamformer. A digitized signal may be shifted using quadrature sampling and sample decimation. Fine shifts in frequency are achieved by means of complex multiplication with an appropriate complex exponential $\exp(j*2*\pi*t*f_0)$, where $f_0$ is the amount of shift in frequency. The amount of frequency downshifting can be varied as a function of time and therefore range. Varying the degree of frequency shifting of the signal with respect to a fixed-frequency bandpass filter results in a time-varying portion of the original signal spectrum being passed. A fixed finite impulse response (FIR) bandpass or low-pass filter is applied to the data to yield a net response equivalent to a time-varying filter.

It is anticipated that the receive beamformer described in Wright, et al. U.S. patent application Ser. No. 08/286,658, filed Aug. 5, 1994, now abandoned and assigned to the assignee of the present invention can be adapted for use with this invention.

Other Applications

It should be understood that the applications discussed above have been provided only by way of example. The present invention can be adapted to a wide range of applications, and is not to be limited to the specific applications discussed in this specification.

For example, the present invention is well suited for use in multiple beam systems, as well as in systems that downshift frequency for off-axis scan lines. Wright, et al. U.S. patent application Ser. No. 08/286,524, filed Aug. 5, 1994, now abandoned and assigned to the assignee of the present invention, describes such systems in detail.

This invention my also be used in conjunction with non-linear contrast agents, as described by B. Schrope, et al. ("Simulated Capillary Blood Flow Measurement Using a Nonlinear Ultrasonic Contrast Agent," Ultrasonic Imaging, 14, 134–152 (1992)). These agents possess a resonant frequency and, when subjected to high pressure intensity at this frequency, will cause acoustic pressure waves to be emitted at the second, or higher, harmonic of the fundamental transmitted frequency. In the receive signal path, echoes at the fundamental frequency are filtered out to produce an image of only the contrast agents—which typically follows closely the flow of blood through the medium of interest. In transmission, the bandwidth of the emitted signal is controlled so that practically no second harmonic energy is transmitted, which would result in echoes being received which would be indistinguishable from the desired second harmonic contrast agent induced signals. The present invention is of particular importance in this application, since it permits a high acoustic pressure to be maintained over a greater depth of field than in a fixed focus system. Maintaining the acoustic pressure at high safe levels is preferred, since at these pressures the second harmonic non-linear generation is most effective. In the present invention one might transmit 3 MHz energy to a deep focus and 3.5 MHz energy to a more shallow focus. In receive, a time-varying filter would first detect signals at 7 MHz and then vary downwards in frequency to detect signals at 6 MHz.

Further Best Mode Details

As described above, a wide variety of waveforms can be used, depending upon the particular application. The following discussion focuses on one preferred embodiment, and is not intended to be limiting.

Figure 16:
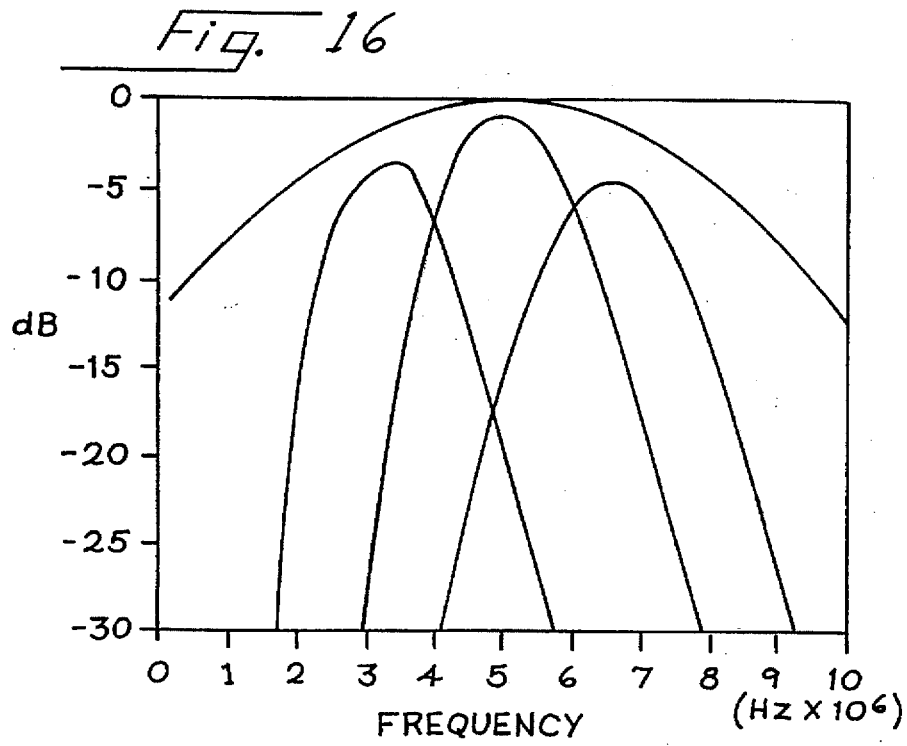
FIG. 16 is a graph of unfiltered and filtered spectra (3, 5, 7 MHz).

For this example the transducer is assumed to be a 5 MHz, 128 element, 0.15 millimeter pitch transducer. The original transmit pulse is a 150% bandwidth Gaussian pulse, and three sections are filtered out at 3, 5, 7 MHz using a Butterworth filter. A Chebyshev, Bessel or digital finite impulse response (FIR) filter may be a suitable alternative. The resulting spectra of the three-filtered sections are shown in FIG. 16. The filter was chosen to have approximately 30% bandwidth (with respect to the center frequency) at the −6 dB points. The bandwidth and number of filter poles are constant. Generally, it is assumed that 3 MHz energy is focused at 140 mm, 5 MHz energy at 90 mm, and 7 MHz energy at 40 mm.

Figure 17:
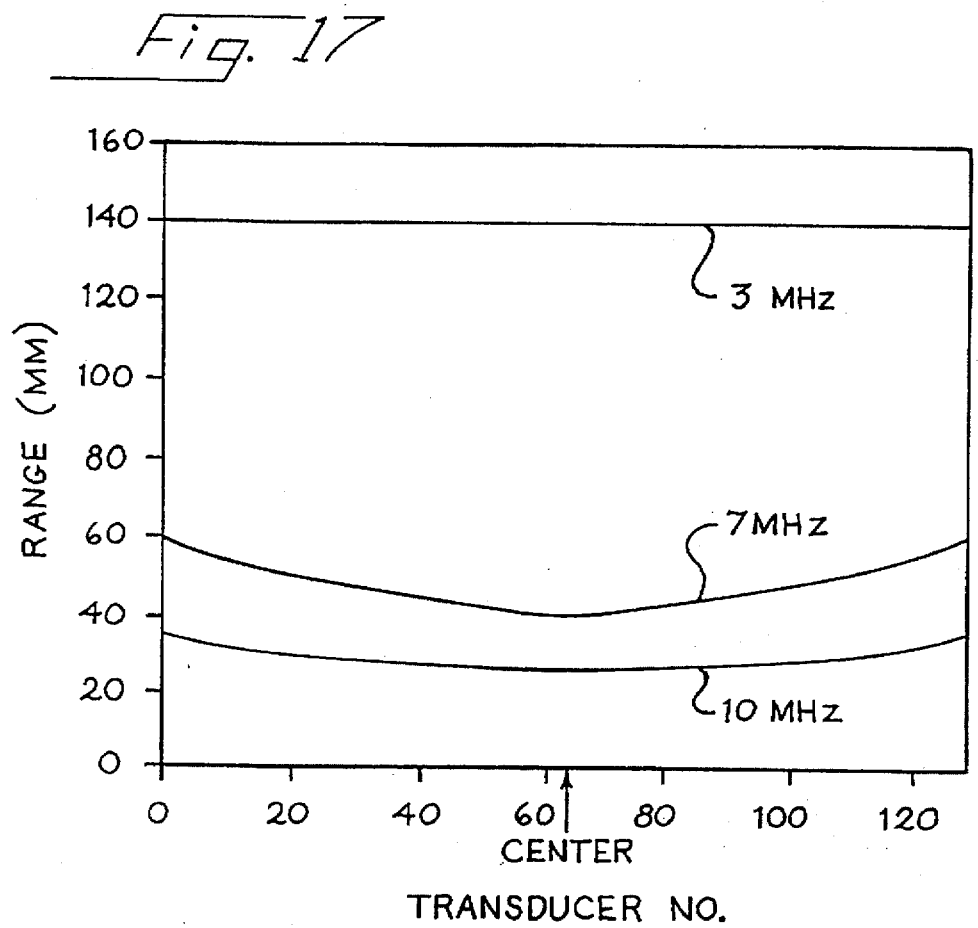
FIG. 17 is a graph showing focal distance versus transducer number for 3, 7 and 10 MHz components.

FIG. 17 shows the variations in focus as a function of frequency and range. At 3 MHz, the entire transducer array is focused at 140 millimeters. At 7 MHz only the center of the array is focused at 40 millimeters. The near focal point at 10 MHz is 28 millimeters.

Figure 18:
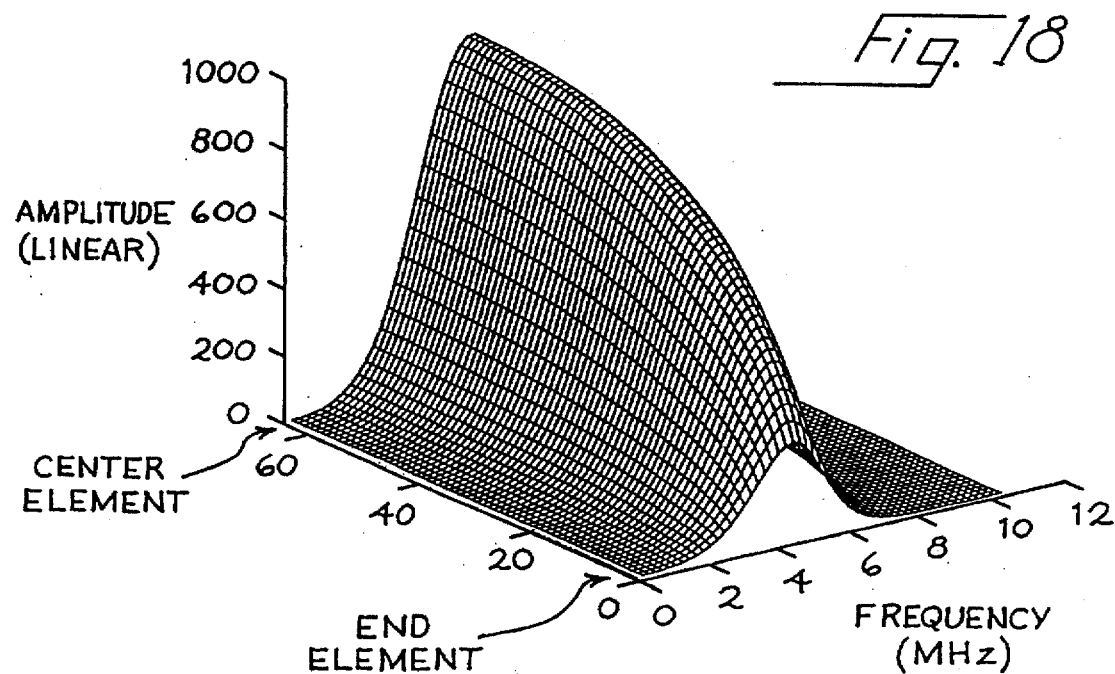
FIG. 18 is a graph of spectra of transmit waveforms for the center through end transducers within the frequency range of 0–10 MHz.
Figure 19:
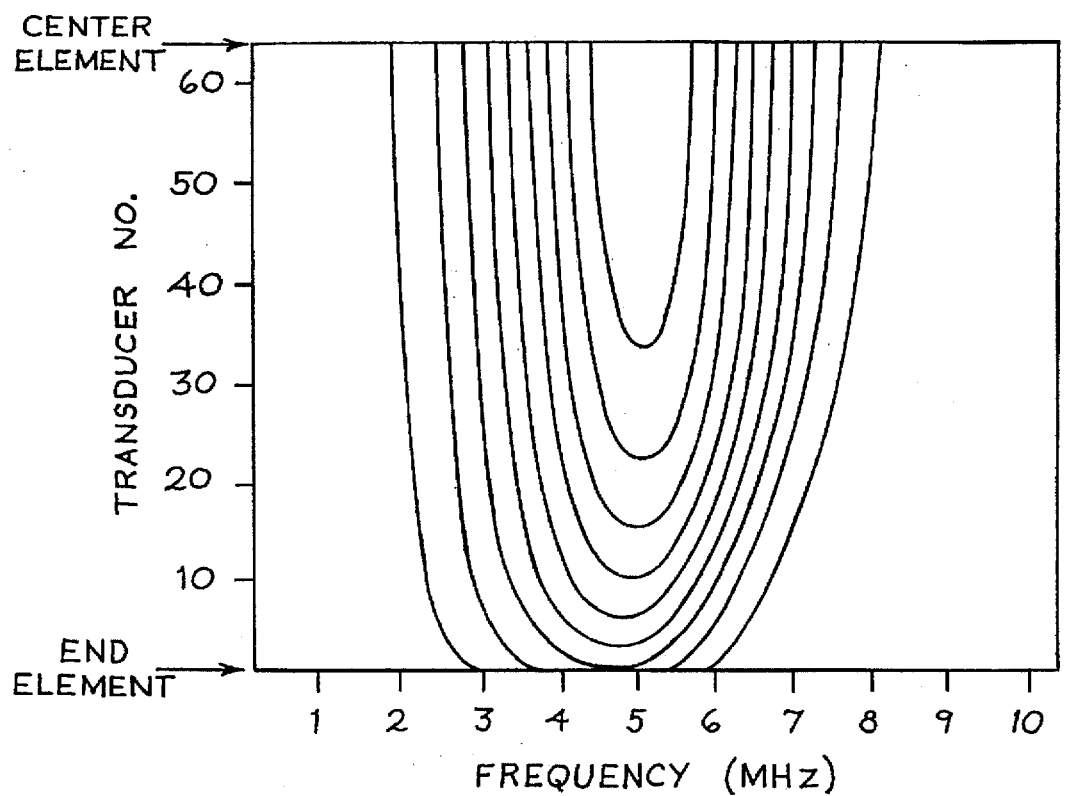
FIG. 19 is a contour plot of the spectra of FIG. 18.

Low-pass filtering was applied to all elements, with more filtering of the end elements as suggested above. The cutoff frequencies across the array of transducer elements varied from 9 MHz at the center of the array to 5 MHz at the end of the array. The element-to-element function for determining the cutoff was linear. FIG. 18 illustrates the spectra of the elements extending from the center to the end of the transducer array. Half circle amplitude apodization has also been applied. The minimum amplitude level at the ends is 0.2, though it could be lowered to further suppress side lobes. FIG. 19 is a contour plot illustrating the data of FIG. 18.

Figure 20:
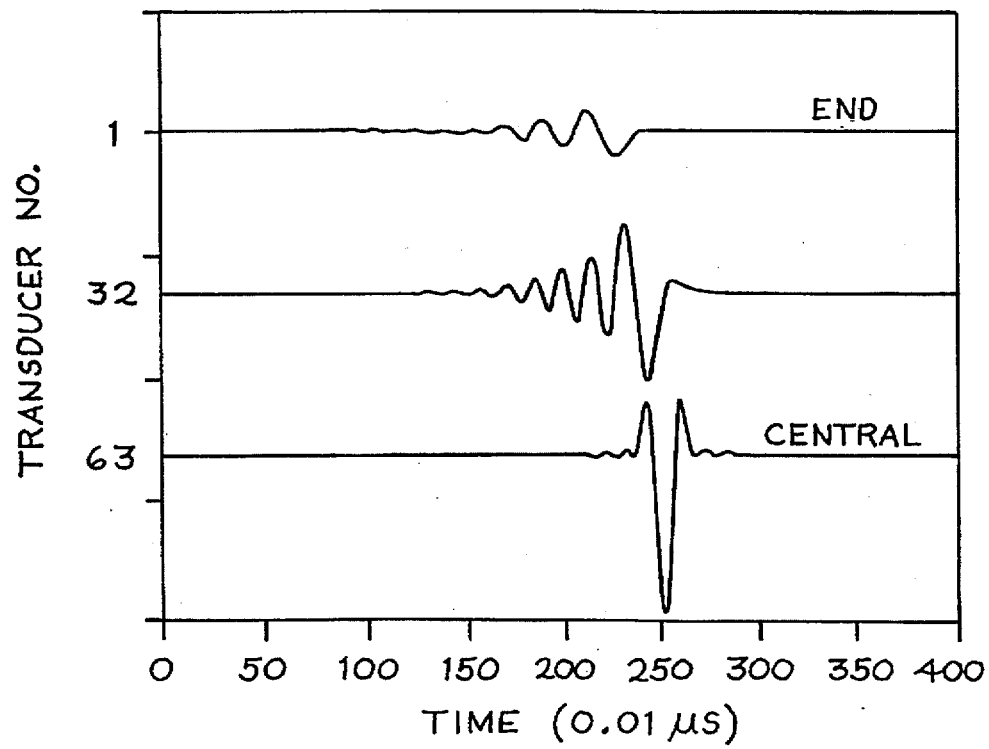
FIG. 20 is a graph showing transmit waveforms for transducers 1, 32 and 63 with no incremental delay.

FIG. 20 illustrates waveforms to be applied to the end transducer, a transducer midway between the end and the center, and the center transducer. A very substantial reduction in ringdown is readily evident. The duration of the pulse is limited more by the near focal zone delay profile than by ringdown.

Figure 21:
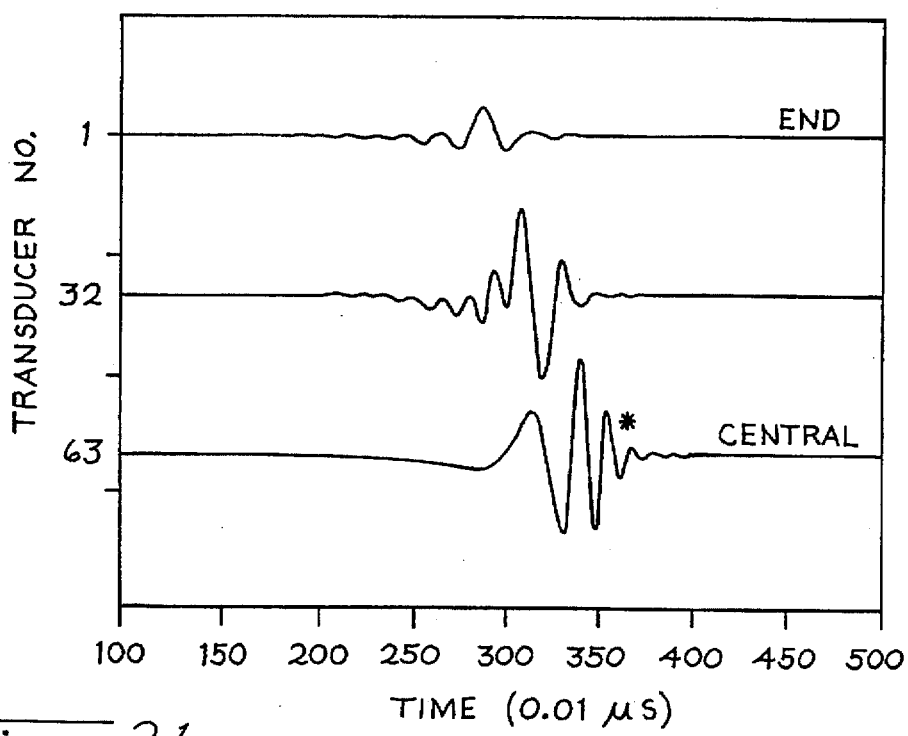
FIG. 21 is a graph of transmit waveforms for transducers 1, 32 and 63 with incremental delay.

FIG. 21 illustrates the result when incremental delays are applied to successive frequency components. In this case the delay is 0.27 microseconds between 3 MHz and 7 MHz. The transfer of high frequency energy toward the temporal waveform center of the central element pulse is evident, as shown by the asterisk. The total duration of the pulses is approximately 1.5 microseconds.

Figure 22:
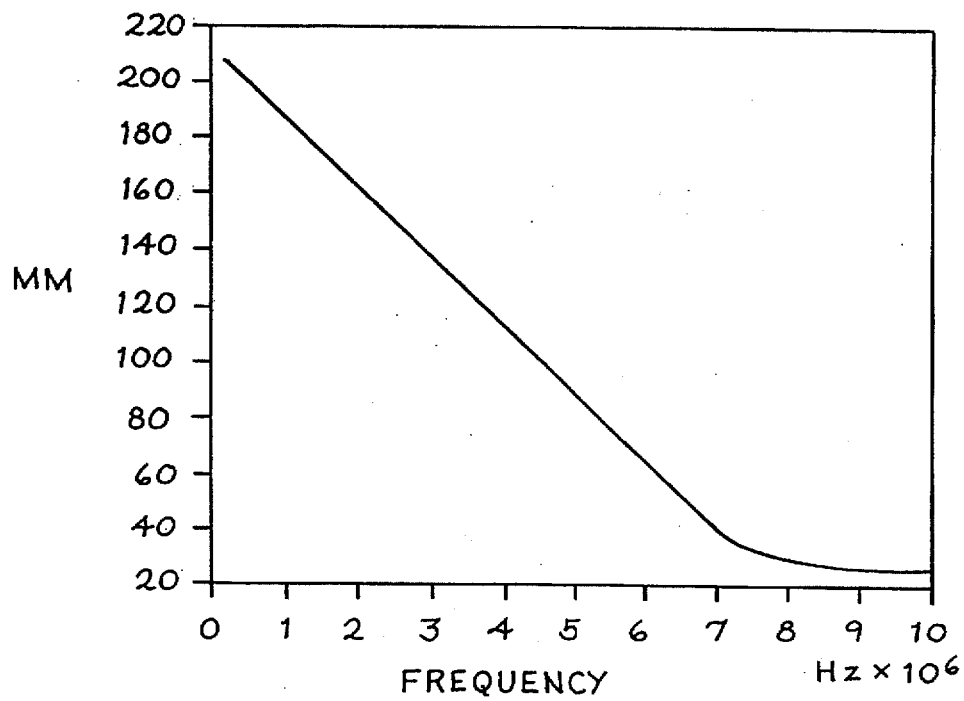
FIG. 22 is a graph showing variation of focal range with frequency, using a far focus of 140 mm, a near focus of 40 mm and a near focal limit of 28 mm.

FIG. 22 illustrates a focal range versus frequency plot. Over the useful range (3–7 MHz) the focal range changes linearly. The receive bandpass filter ideally starts at a center frequency of 7 MHz and continues at 7 MHz until t=2·40 mm/c. Thereafter, the center frequency decreases with range linearly until it reaches 3 MHz at t=2·140 mm/c. At that point the downward ramp stops and remains at 3 MHz. Level regions at the beginning and end of the scan line minimize the loss of useful signal. The slope may be modified in practice to accommodate the frequency downshift versus time due to body attenuation. Although the variation of focal range with respect to frequency is linear over the primary operating range in FIG. 22, other functions describing the relationship between focal range and frequency, which may result in better overall performance, may be derived by analysis or experimentation. As an example, since focusing delays are approximately related to the inverse of the focal range, it may be preferable to make focal range an inverse function of frequency so that range change is greatest where the resulting delay changes are smallest.

FIG. 23 illustrates a graph of an ultrasonic scan line that is focused so that after bandpass filtering it follows an arc of radius 500 mm.

In general, the maximum intensity should be at the deeper focal zones, where the signal-to-noise ratio is the lowest. This can be accomplished by skewing the Gaussian spectrum described above by low-pass filtering it to emphasize low frequency energy at the expense of 5 and 7 MHz energy. A suitable filter is a 4 pole, 3.5 MHz Butterworth low-pass filter. When such a filtered Gaussian was used, the maximum intensity was achieved at 140 mm.

More complicated filter approaches can be used. For example, in a situation where the peak intensity is at the 5 MHz focus, one may replace the pure Gaussian spectrum discussed above with one having a flat top and a Gaussian-like roll-off. See FIG. 24. In this way good performance can be maintained at both 3 MHz and 7 MHz.

The attached appendix provides a listing of digitized sample values of 16 transmit waveforms suitable for use for transducer elements 0, 4, 8 . . . 60 of the linear array described above, focused perpendicularly to the transducer array. The waveforms for intermediate transducer elements may be found using the interpolation scheme described above. Also, the waveforms for elements 67 to 127 may be found from the mirror image of the data shown for elements 0 to 60, i.e., Channel 127=Channel 0, Channel 123=Channel 4, etc. Channels 61–66 may use the values for Channel 60 since the variation among center channels is negligible. See the difference between Channels 60 and 56. In the appendix, row A lists the transducer numbers 0, 4, 8 . . . 3C(Hex), rows B and C list the delay values for each respective waveform in hex, and rows 00–3F list 64 successive values for each waveform, when read as a column. The delay values of rows B and C assume 200(Hex) is zero, and 0–1FF(Hex) are consecutive negative integers. The waveform values of rows 00–3F are linear, with 80(Hex) equal to zero, and 81–FF (Hex) equal to positive integers and 0–7F(Hex) equal to negative integers. The appendix assumes a clock rate of 40 MHz. In this case 64 memory samples are just sufficient. In a commercial design, considerable flexibility is offered when the memory size is increased to 128 samples.

Conclusion

The systems described above provide a number of important advantages. Since the transmit beamformers provide a line focus rather than a point focus, there is a reduced requirement for user fine tuning. This can reduce or eliminate the need for a user to select the correct focal depth or to resort to multi-zone imaging. These systems can give highly advantageous resolution at high frame rates without resorting to multi-zone techniques. By eliminating or reducing the need for multi-zone techniques, frame rates are increased and image artifact problems associated with the need to combine images are reduced. There is the potential for increased net transmitted power without exceeding peak intensity limits in view of the use of a line focus.

Of course, it should be understood that many changes and modifications can be made to the preferred embodiments described above. This invention is not limited to use with ultrasonic beamformers, but can also be adapted for use in sonar, radar, and other applications. It is therefore intended that the foregoing detailed description be regarded as illustrative rather than limiting, and that it be understood that it is the following claims, including all equivalents, that are intended to define the scope of this invention.

| ROW A | 00 | 04 | 08 | 0C | 10 | 14 | 18 | 1C | 20 | 24 | 28 | 2C | 30 | 34 | 38 | 3C |
|---|---|---|---|---|---|---|---|---|---|---|---|---|---|---|---|---|
| B | 1E6 |  | 1E2 |  | 1DE |  | 1DA |  | 1D6 |  | 1D5 |  | 1D5 |  | 1D5 |  |
| C |  | 1E4 |  | 1E0 |  | 1DC |  | 1D8 |  | 1D6 |  | 1D5 |  | 1D5 |  | 1D5 |
| ROW 00 | 82 | 81 | 80 | 80 | 7F | 7E | 7D | 7D | 7C | 7C | 7C | 7C | 7C | 7C | 7C | 7C |
| 01 | 7F | 7E | 7E | 7E | 7E | 7D | 7D | 7D | 7C | 7C | 7C | 7C | 7C | 7C | 7C | 7C |
| 02 | 7C | 7C | 7C | 7D | 7D | 7D | 7D | 7C | 7C | 7C | 7B | 7B | 7B | 7B | 7B | 7B |
| 03 | 7D | 7D | 7E | 7E | 7E | 7E | 7D | 7C | 7B | 7B | 7B | 7B | 7B | 7B | 7B | 7B |
| 04 | 82 | 82 | 81 | 80 | 7F | 7E | 7D | 7B | 7B | 7B | 7B | 7B | 7B | 7B | 7B | 7A |
| 05 | 84 | 83 | 82 | 80 | 7E | 7D | 7C | 7B | 7A | 7A | 7A | 7A | 7A | 7A | 7A | 7A |

-continued

| | | | | | | | | | | | | | | | | |
|---|---|---|---|---|---|---|---|---|---|---|---|---|---|---|---|---|
| 06 | 7F | 7F | 7E | 7D | 7C | 7B | 7B | 7A | 7A | 7A | 7A | 7A | 7A | 7A | 7A | 7A |
| 07 | 79 | 79 | 79 | 79 | 7A | 7A | 7B | 7B | 7B | 7A | 7A | 7A | 7A | 7A | 7A | 7A |
| 08 | 7A | 79 | 79 | 7A | 7B | 7B | 7B | 7B | 7B | 7B | 7B | 7B | 7A | 7A | 7A | 7A |
| 09 | 60 | 80 | 80 | 7F | 7E | 7D | 7C | 7B | 7B | 7B | 7B | 7B | 7B | 7B | 7B | 7B |
| 0A | 85 | 85 | 84 | 81 | 7F | 7D | 7B | 7B | 7B | 7B | 7C | 7B | 7B | 7B | 7B | 7B |
| 0B | 81 | 80 | 7F | 7E | 7C | 7B | 7A | 7A | 7C | 7C | 7C | 7C | 7C | 7C | 7C | 7C |
| 0C | 78 | 76 | 76 | 76 | 77 | 78 | 79 | 7B | 7D | 7C | 7D | 7D | 7D | 7D | 7C | 7C |
| 0D | 76 | 74 | 74 | 75 | 77 | 79 | 7B | 7D | 7E | 7D | 7E | 7E | 7E | 7D | 7D | 7D |
| 0E | 7D | 7D | 7C | 7C | 7D | 7D | 7E | 7F | 7F | 7F | 7F | 7F | 7F | 7F | 7F | 7F |
| 0F | 83 | 85 | 86 | 84 | 82 | 80 | 7F | 7F | 80 | 80 | 81 | 80 | 80 | 80 | 80 | 80 |
| 10 | 83 | 83 | 83 | 82 | 80 | 7E | 7D | 7E | 80 | 81 | 82 | 82 | 82 | 81 | 81 | 81 |
| 11 | 7C | 78 | 77 | 77 | 78 | 79 | 7B | 7E | 82 | 82 | 83 | 83 | 83 | 83 | 83 | 83 |
| 12 | 76 | 72 | 70 | 71 | 74 | 78 | 7D | 81 | 83 | 84 | 85 | 85 | 85 | 85 | 85 | 85 |
| 13 | 77 | 78 | 78 | 79 | 7C | 7F | 83 | 86 | 88 | 86 | 87 | 87 | 87 | 86 | 86 | 86 |
| 14 | 7E | 82 | 86 | 88 | 88 | 88 | 88 | 88 | 88 | 89 | 89 | 89 | 88 | 88 | 88 | 88 |
| 15 | 84 | 86 | 89 | 8B | 8A | 88 | 86 | 86 | 88 | 8A | 8B | 8B | 8B | 8A | 8A | 8A |
| 16 | 83 | 82 | 80 | 7F | 7F | 7F | 81 | 84 | 89 | 8B | 8D | 8D | 8C | 8C | 8C | 8C |
| 17 | 7D | 79 | 75 | 73 | 74 | 79 | 7F | 87 | 8D | 8C | 6E | 8E | 8E | 8E | 8E | 8E |
| 18 | 77 | 75 | 75 | 77 | 7A | 80 | 88 | 8E | 92 | 8F | 90 | 90 | 90 | 90 | 90 | 90 |
| 19 | 78 | 7A | 80 | 87 | 8D | 91 | 94 | 95 | 94 | 92 | 92 | 92 | 91 | 92 | 92 | 92 |
| 1A | 80 | 85 | 8C | 92 | 97 | 98 | 96 | 92 | 90 | 93 | 93 | 93 | 93 | 93 | 93 | 93 |
| 1B | 88 | 8C | 8E | 8E | 8E | 8C | 8B | 8A | 8C | 92 | 92 | 93 | 93 | 93 | 93 | 93 |
| 1C | 89 | 89 | 86 | 81 | 7D | 7D | 81 | 88 | 8E | 8F | 90 | 92 | 92 | 92 | 93 | 93 |
| 1D | 82 | 7F | 7C | 7A | 7A | 7F | 88 | 91 | 94 | 8E | 8D | 8F | 90 | 90 | 91 | 91 |
| 1E | 7A | 78 | 79 | 80 | 8A | 93 | 9B | 9C | 9F | 8F | 8A | 8B | 8C | 8D | 8D | 8D |
| 1F | 79 | 7D | 84 | 90 | 9C | A4 | A4 | 9A | 88 | 8D | 85 | 85 | 86 | 87 | 87 | 87 |
| 20 | 82 | 8B | 95 | 9C | A0 | 9E | 94 | 85 | 74 | 83 | 7B | 7D | 7E | 7E | 7F | 7F |
| 21 | 8E | 97 | 9C | 9B | 93 | 87 | 7A | 70 | 67 | 72 | 6C | 71 | 73 | 74 | 74 | 74 |
| 22 | 94 | 97 | 94 | 8C | 82 | 77 | 71 | 6E | 68 | 63 | 5D | 62 | 66 | 67 | 68 | 68 |
| 23 | 8E | 8B | 83 | 7C | 7A | 7C | 7F | 7B | 6A | 5C | 53 | 55 | 58 | 5A | 5B | 5B |
| 24 | 82 | 7C | 79 | 7A | 83 | 8D | 8D | 7A | 5A | 5A | 50 | 4D | 4E | 4F | 50 | 4F |
| 25 | 79 | 79 | 7F | 8A | 94 | 93 | 80 | 5B | 3D | 53 | 50 | 4D | 4B | 4A | 4A | 4A |
| 26 | 7C | 85 | 92 | 9D | 9A | 81 | 57 | 32 | 35 | 49 | 56 | 56 | 52 | 50 | 4F | 4E |
| 27 | 8A | 98 | A2 | 9E | 86 | 5B | 30 | 29 | 5F | 4E | 6C | 6B | 67 | 63 | 61 | 61 |
| 28 | 9A | A3 | 9E | 85 | 5C | 34 | 29 | 54 | AE | 78 | 9A | 8E | 89 | 84 | 82 | 82 |
| 29 | 9F | 9A | 82 | 5B | 34 | 27 | 4B | 9E | EF | C0 | D5 | BE | B4 | AF | AC | AC |
| 2A | 92 | 7C | 59 | 37 | 29 | 44 | 8A | DB | F5 | F9 | E7 | DB | D5 | D3 | D3 | D3 |
| 2B | 77 | 59 | 3A | 2E | 45 | 80 | C8 | EC | C1 | F4 | E1 | EC | E9 | E6 | E5 | E6 |
| 2C | 5C | 41 | 36 | 48 | 7B | BC | E5 | CE | 79 | AF | 90 | BA | CB | D0 | D3 | D4 |
| 2D | 4D | 42 | 50 | 79 | B1 | DA | D3 | 94 | 46 | 59 | 39 | 63 | 83 | 93 | 99 | 9A |
| 2E | 51 | 5A | 7B | A9 | CE | CE | A0 | 5C | 3A | 2B | 17 | 1C | 33 | 45 | 4D | 4D |
| 2F | 66 | 7E | A2 | C2 | C7 | A6 | 6C | 41 | 4E | 35 | 39 | 16 | 0E | 13 | 16 | 16 |
| 30 | 81 | 9D | B7 | BE | A7 | 79 | 4F | 4B | 73 | 5F | 78 | 50 | 2E | 1E | 19 | 18 |
| 31 | 96 | AB | B3 | A4 | 81 | 5B | 50 | 6A | 91 | 87 | A2 | 99 | 7C | 63 | 57 | 57 |
| 32 | A0 | A8 | 9F | 85 | 66 | 57 | 64 | 86 | 9A | 9B | A5 | B8 | BA | AF | A6 | A7 |
| 33 | 9D | 99 | 87 | 6E | 5F | 64 | 7C | 92 | 90 | 9B | 93 | A6 | BE | CB | CE | CE |
| 34 | 92 | 86 | 74 | 66 | 67 | 77 | 8B | 8F | 80 | 8C | 80 | 82 | 94 | A8 | B4 | B4 |
| 35 | 85 | 78 | 6D | 6B | 74 | 84 | 8D | 85 | 78 | 7B | 74 | 6F | 6B | 72 | 79 | 79 |
| 36 | 7B | 72 | 6F | 74 | 80 | 88 | 86 | 7C | 73 | 72 | 70 | 64 | 59 | 56 | 55 | 55 |
| 37 | 77 | 73 | 75 | 7D | 85 | 86 | 7F | 79 | 7B | 76 | 78 | 78 | 74 | 69 | 61 | 61 |
| 38 | 77 | 77 | 7C | 82 | 84 | 81 | 7C | 7B | 7F | 7E | 80 | 7E | 83 | 83 | 80 | 80 |
| 39 | 79 | 7C | 80 | 83 | 82 | 7E | 7C | 7E | 81 | 82 | 84 | 83 | 85 | 8B | 8F | 8F |
| 3A | 7C | 7F | 81 | 82 | 7F | 7D | 7D | 80 | 80 | 82 | 82 | 84 | 82 | 84 | 88 | 88 |
| 3B | 7F | 80 | 81 | 80 | 7E | 7D | 7E | 80 | 7F | 80 | 7F | 81 | 80 | 7E | 7D | 7D |
| 3C | 80 | 80 | 80 | 7E | 7D | 7E | 7F | 7F | 7F | 7F | 7E | 7E | 7F | 7E | 7B | 7B |
| 3D | 80 | 7F | 7F | 7E | 7E | 7F | 7F | 7F | 80 | 7F | 7F | 7E | 7E | 7F | 7F | 7F |
| 3E | 7F | 7F | 7E | 7E | 7F | 7F | 80 | 80 | 80 | 80 | 80 | 7F | 7F | 80 | 81 | 81 |
| 3F | 7F | 7E | 7E | 7E | 7F | 80 | 80 | 80 | 80 | 80 | 81 | 81 | 80 | 80 | 80 | 80 |

I claim:

1. In a transmit beamformer for a medical ultrasound imaging system, said imagining system comprising a plurality of transducers, each transducer responsive to a respective transmit waveform to produce a respective transducer waveform, the improvement comprising:

a transmit waveform generator which generates the transmit waveforms, each of at least a plurality of the transmit waveforms comprising at least first and second frequency components included in a single burst of energy, said first frequency components timed to cause corresponding first frequency components of the transducer waveforms to focus at a first depth, and said second frequency components timed to cause corresponding second frequency components of the transducer waveforms to focus at a second depth, less than the first depth, said transmit waveform generator generating each of said transmit waveforms as a function of a respective square wave burst.

2. The invention of claim 1 wherein the first frequency component of one of the transmit waveforms is characterized by a lower frequency than the second frequency component of said transmit waveform.

3. The invention of claim 1 wherein the plurality of transducers includes all of the transducers of the transmit beamformer.

4. The invention of claim 1 wherein each transmit waveform comprises more than two frequency components, wherein progressively lower frequency components of the transmit waveforms are timed to cause corresponding progressively lower frequency components of the transducer waveforms to focus at progressively greater depths.

5. The invention of claim 4 wherein the frequency components of the transmit waveforms are timed to cause corresponding frequency components of the transducer waveforms to focus along a straight line.

6. The invention of claim 4 wherein the frequency components of the transmit waveforms are timed to cause corresponding frequency components of the transducer waveforms to focus along a curved line.

7. The invention of claim 1 wherein the first frequency components comprise components at 3 MHz, and wherein the second frequency components comprise components at 7 MHz.

8. The invention of claim 1 wherein the plurality of transmit waveforms comprises a central transmit waveform associated with a central one of the transducers, and wherein the first frequency components of the central transmit waveform occur earlier in time than the second frequency components of the central transmit waveform.

9. The invention of claim 1 wherein the first and second frequency components are weighted to enhance amplitude of the ultrasonic waveforms at the first depth.

10. The invention of claim 1 wherein the transducers comprise central transducers and end transducers, wherein the second depth comprises a plurality of depth values, and wherein the depth value for the second components associated with the end transducers is greater than the depth value for the second components associated with the central transducers.

11. The invention of claim 1 wherein the transducer waveforms are ultrasonic waveforms.

12. The invention of claim 1 wherein the first and second frequency components of each transmit waveform are included in a continuously varying portion of the respective transmit waveform.

13. In a transmit beamformer for a medical ultrasound imaging system, said imaging system comprising a plurality of transducers, each transducer responsive to a respective transmit waveform to produce a respective transducer waveform, the improvement comprising:

a transmit waveform generator which generates the transmit waveforms, each of at least a plurality of the transmit waveforms comprising at least first and second frequency components included in a continuously varying portion of the respective transmit waveform, said first frequency components timed to cause corresponding first frequency components of the transducer waveforms to focus at a first region, and said second frequency components timed to cause corresponding second frequency components of the transducer waveforms to focus at a second region, spaced from the first region.

14. The invention of claim 1 in combination with a receive beamformer coupled to the transducers, said receive beamformer comprising a time varying frequency filter coupled to the transducers to process arriving signals from the transducers.

15. The invention of claim 14 wherein the receive beamformer comprises means for adjusting the filter in real time to emphasize a changing frequency of the arriving signals.

16. The invention of claim 1 wherein said at least a plurality of transmit waveforms each comprise a multiplicity of frequency components included in a single burst of energy, each of said frequency components timed to cause corresponding frequency components of the transducer waveforms to focus at a separate respective depth.

17. The invention of claim 16 wherein the frequency components of the transducer waveforms focus along a continuous line.

18. The invention of claim 1 wherein the transducers comprise a central transducer and a plurality of end transducers, and wherein the transmit waveforms cause at least some higher frequency components of the transducer waveforms to focus at a greater depth for the end transducers than for the center transducer.

19. The invention of claim 1 wherein the transmit waveforms cause at least some of the lower frequency components of the transducer waveforms to be enhanced in amplitude to increase the energy focused at greater depths.

20. The invention of claim 1 wherein the transducers comprise a linear phased array.

21. The invention of claim 1 wherein the transducers are arranged in an array and wherein said first depth varies progressively across the array.

22. The invention of claim 21 wherein said first depth varies monotonically across the array from a central transducer to an edge transducer.

23. The invention of claim 14 wherein the time-varying filter processes arriving signals at frequencies associated with harmonics of the first and second frequency components.

24. The invention of claim 14 wherein the time-varying filter processes arriving signals at frequencies substantially equal to twice that of the first frequency component at a first time and at frequencies substantially equal to twice that of the second frequency component at a second time.

25. The invention of claim 14 or 23 or 24 wherein the time-varying filter processes arriving signals at frequencies at which substantially no energy is transmitted in the transducer waveforms.

26. The invention of claim 16 wherein the depths at which the respective frequency components focus vary monotonically with frequency.

27. The invention of claim 1 wherein each of the transmit waveforms is characterized by a respective Fourier transform that is bell-shaped.

28. The invention of claim 1 wherein each of the transmit waveforms is characterized by a respective Fourier transform that is generally Gaussian in shape.

29. The invention of claim 1 or 23 or 24 wherein the transmit waveforms are selected such that practically no second harmonic energy is transmitted.

30. The invention of claim 14 or 15 wherein the time varying frequency filter comprises an analog filter.

31. The invention of claim 14 or 15 wherein the time varying frequency filter comprises a digital filter.

32. The invention of claim 31 wherein the digital filter comprises a complex processor.

33. The invention of claim 13 wherein said transmit waveform generator generates each of said transmit waveforms as a function of a respective square wave burst.

34. In a transmit beamformer for a medical ultrasound imaging system, said imaging system comprising a plurality of transducers, each transducer responsive to a respective transmit waveform to produce a respective transducer waveform, the improvement comprising:

a transmit waveform generator which generates the transmit waveforms, each of at least a plurality of the transmit waveforms comprising at least first and second frequency components included in a single burst of energy, said first frequency components timed to cause corresponding first frequency components of the transducer waveforms to focus at a first region, and said second frequency components timed to cause corresponding second frequency components of the transducer waveforms to focus at a second region, said first region spaced from the second region.

35. The invention of claim 34 wherein the first frequency component of one of the transmit waveforms is characterized by a lower frequency than the second frequency component of said transmit waveform.

36. The invention of claim 34 wherein the plurality of transducers includes all of the transducers of the transmit beamformer.

37. The invention of claim 34 wherein each transmit waveform comprises more than two frequency components, wherein progressively lower frequency components of the transmit waveforms are timed to cause corresponding progressively lower frequency components of the transducer waveforms to focus at progressively spaced regions along a line.

38. The invention of claim 37 wherein the frequency components of the transmit waveforms are timed to cause the line to be straight.

39. The invention of claim 37 wherein the frequency components of the transmit waveforms are timed to cause the line to be curved.

40. The invention of claim 34 wherein the transmit waveform generator comprises:
a memory which stores at least one digitally encoded waveform;
a digital-to-analog converter coupled to the memory; and
a memory controller coupled to the memory to supply the digitally encoded waveform to the digital-to-analog converter;
said digital-to-analog converter generating at least one analog waveform corresponding to the digitally encoded waveform, said analog waveform corresponding to at least a selected one of the transmit waveforms.

41. The invention of claim 40 wherein the transmit waveform generator further comprises a delay memory comprising a plurality of delay values, and wherein the memory controller is responsive to a selectable one of the delay values.

42. The invention of claim 40 wherein the transmit waveform generator further comprises an interpolator interposed between the memory and the digital-to-analog converter to interpolate between selected ones of the digitally encoded waveforms.

43. The invention of claim 42 wherein the interpolator comprises at least one shifter responsive to a selectable digitally encoded waveform to generate a shifted waveform, and a summer responsive to the shifted waveform.

44. The invention of claim 40 wherein the memory stores a first digitally encoded waveform and a delta value that defines a differential between an additional digitally encoded waveform and the first digitally encoded waveform.

45. The invention of claim 34 wherein the first frequency components comprise components at 3 MHz, and wherein the second frequency components comprise components at 7 MHz.

46. The invention of claim 34 wherein the plurality of transmit waveforms comprises a central transmit waveform associated with a central one of the transducers, and wherein the first frequency components of the central transmit waveform occur earlier in time than the second frequency components of the central transmit waveform.

47. The invention of claim 34 wherein the first and second frequency components are weighted to enhance amplitude of the ultrasonic waveforms at the first region.

48. The invention of claim 34 wherein the transducers comprise central transducers and end transducers, wherein the second region comprises a plurality of depth values, and wherein the depth value for the second components associated with the end transducers is greater than the depth value for the second components associated with the central transducers.

49. The invention of claim 34 wherein the transducer waveforms are ultrasonic waveforms.

50. The invention of claim 34 wherein the first and second frequency components of each transmit waveform are included in a continuously varying portion of the respective transmit waveform.

51. The invention of claim 34 in combination with a receive beamformer coupled to the transducers, said receive beamformer comprising a time varying frequency filter coupled to the transducers to process arriving signals from the transducers.

52. The invention of claim 51 wherein the receive beamformer comprises means for adjusting the filter in real time to emphasize a changing frequency of the arriving signals.

53. The invention of claim 34 wherein said at least a plurality of transmit waveforms each comprise a multiplicity of frequency components included in a single burst of energy, each of said frequency components timed to cause corresponding frequency components of the transducer waveforms to focus at a separate respective region.

54. The invention of claim 53 wherein the frequency components of the transducer waveforms focus along a continuous line.

55. The invention of claim 34 wherein the transducers comprise a central transducer and a plurality of end transducers, and wherein the transmit waveforms cause at least some higher frequency components of the transducer waveforms to focus at a greater depth for the end transducers than for the center transducer.

56. The invention of claim 34 wherein the transmit waveforms cause at least some of the lower frequency components of the transducer waveforms to be enhanced in amplitude to increase the energy focused at greater depths.

57. The invention of claim 34 wherein the frequency components of the transmit waveforms are more smoothly varying than square waves.

58. The invention of claim 34 wherein the transmit waveform generator comprises a memory which stores a plurality of digitally encoded waveforms, and wherein each of the digitally encoded waveforms encodes both the first and the second frequency components for a respective one of the transmit waveforms.

59. The invention of claim 34 wherein the transducers comprise a linear phased array.

60. The invention of claim 34 wherein each of the transmit waveforms is characterized by a respective frequency domain function having a peak value associated with a selected frequency and a monotonic decrease with frequency away from the peak value.

61. The invention of claim 51 wherein the time-varying filter processes arriving signals at frequencies associated with harmonics of the first and second frequency components.

62. The invention of claim 51 wherein the time-varying filter processes arriving signals at frequencies substantially equal to twice that of the first frequency component at a first time and at frequencies substantially equal to twice that of the second frequency component at a second time.

63. The invention of claim 51 or 61 or 62 wherein the time-varying filter processes arriving signals at frequencies at which substantially no energy is transmitted in the transducer waveforms.

64. The invention of claim 34 wherein each of the transmit waveforms is characterized by a respective Fourier transform that is bell-shaped.

65. The invention of claim 34 wherein each of the transmit waveforms is characterized by a respective Fourier transform that is generally Gaussian in shape.

66. The invention of claim 34 or 61 or 62 wherein the transmit waveforms are selected such that practically no second harmonic energy is transmitted.

67. The invention of claim 51 or 52 wherein the time varying frequency filter comprises an analog filter.

68. The invention of claim 51 or 52 wherein the time varying frequency filter comprises a digital filter.

69. The invention of claim 68 wherein the digital filter comprises a complex processor.

70. The invention of claim 34 wherein the plurality of transducers comprises an end transducer and a central transducer, and wherein the transmit waveform associated with the end transducer comprises a substantially reduced high-frequency component as compared to the transmit waveform associated with the central transducer.

71. The invention of claim 1 or 13 or 34 wherein the transducers comprise central transducers and transducers, wherein the transmit waveforms for the central transducers are limited to a first frequency range, wherein the transmit waveforms for the end transducers are limited to a second frequency range, and wherein the first frequency range extends to higher frequencies than the second frequency range.

72. The invention of claim 34 wherein said transmit waveform generator generates each of said transmit waveforms as a function of a respective square wave burst.

73. The invention of claim 1 or 71 or 72 wherein said transmit waveform generator comprises means for low-pass-filtering the square wave bursts.

74. The invention of claim 13 or 34 wherein the first and second regions are spaced from one another in azimuth.

75. The invention of claim 13 or 34 wherein the first and second regions are spaced from one another in range.

* * * * *

UNITED STATES PATENT AND TRADEMARK OFFICE
CERTIFICATE OF CORRECTION

PATENT NO.  : 5,696,737
DATED       : December 9, 1997
INVENTOR(S) : John A. Hossack et al.

It is certified that error appears in the above-identified patent and that said Letters Patent is hereby corrected as shown below:

On the Title Page

Item [56], "OTHER PUBLICATIONS" replace "Unversity" with --University--.

In column 6, line 57, replace "my" with --may--.

In column 6, line 64, replace "my" with --may--.

In column 8, line 51, replace "3" with --13--.

UNITED STATES PATENT AND TRADEMARK OFFICE
CERTIFICATE OF CORRECTION

PATENT NO. : 5,696,737
DATED : December 9, 1997
INVENTOR(S) : John A. Hossack et al.

It is certified that error appears in the above-identified patent and that said Letters Patent is hereby corrected as shown below:

In column 9, line 44, replace "+1  +2  +4  +1  +2  +4" with --÷1  ÷2  ÷4  ÷1  ÷2  ÷4--.

In column 11, line 48, replace "my" with --may--.

In column 11, line 53, replace "A-time" with --A time--.

In column 12, line 20, replace "my" with --may--.

Signed and Sealed this

Fifteenth Day of June, 1999

Attest:

Q. TODD DICKINSON

*Attesting Officer*    *Acting Commissioner of Patents and Trademarks*